United States Patent
Bayer et al.

(10) Patent No.: US 10,420,893 B2
(45) Date of Patent: Sep. 24, 2019

(54) DRUG DELIVERY DEVICE

(71) Applicant: Sanofi, Paris (FR)

(72) Inventors: Stefan Bayer, Würselen (DE); Philippe Blank, Düsseldorf (DE); Wolfgang Pelzer, Kreuzau (DE); Michael Pfoser, Kohlscheid (DE); Björn Wilden, Simmerath (DE); Philipp Zeitz, Aachen (DE)

(73) Assignee: Sanofi, Paris (FR)

( * ) Notice: Subject to any disclaimer, the term of this patent is extended or adjusted under 35 U.S.C. 154(b) by 576 days.

(21) Appl. No.: 14/916,836

(22) PCT Filed: Sep. 8, 2014

(86) PCT No.: PCT/EP2014/069038
§ 371 (c)(1),
(2) Date: Mar. 4, 2016

(87) PCT Pub. No.: WO2015/036347
PCT Pub. Date: Mar. 19, 2015

(65) Prior Publication Data
US 2016/0193421 A1  Jul. 7, 2016

(30) Foreign Application Priority Data
Sep. 10, 2013  (EP) .................................. 13183656

(51) Int. Cl.
| | | |
|---|---|---|
| *A61M 5/315* | (2006.01) | |
| *A61M 5/24* | (2006.01) | |
| *A61M 5/28* | (2006.01) | |

(52) U.S. Cl.
CPC .......... *A61M 5/31541* (2013.01); *A61M 5/24* (2013.01); *A61M 5/28* (2013.01);
(Continued)

(58) Field of Classification Search
CPC ........ A61M 2005/202; A61M 5/31591; A61M 5/31593; A61M 5/2448; A61M 5/2033;
(Continued)

(56) References Cited

U.S. PATENT DOCUMENTS

| | | | | |
|---|---|---|---|---|
| 1,512,294 A | * | 10/1924 | Marcy ..................... | A61M 5/24 222/326 |
| 5,112,317 A | * | 5/1992 | Michel .................... | A61M 5/24 222/386 |

(Continued)

FOREIGN PATENT DOCUMENTS

| | | |
|---|---|---|
| WO | WO2012/067584 | 5/2012 |
| WO | WO2012/152666 | 11/2012 |

OTHER PUBLICATIONS

International Search Report and Written Opinion in International Application No. PCT/EP2014/069038, dated Mar. 15, 2016, 8 pages.
(Continued)

*Primary Examiner* — Theodore J Stigell
*Assistant Examiner* — Hong-Van N Trinh
(74) *Attorney, Agent, or Firm* — Fish & Richardson P.C.

(57) ABSTRACT

A drug delivery device for dispensing of a dose of a medicament includes an elongated body extending in an axial direction, a cartridge holder to accommodate a cartridge at least partially filled with the medicament and having an axially displaceable piston, and a piston rod to operably engage with the piston of the cartridge to displace the piston in axial distal direction. The drug delivery device further includes a coupling member connected with the cartridge holder and being axially displaceably arranged in the body for retracting the cartridge holder into the body during setting of a dose.

17 Claims, 10 Drawing Sheets

(52) U.S. Cl.
CPC ...... *A61M 5/3158* (2013.01); *A61M 5/31591* (2013.01); *A61M 2005/2403* (2013.01); *A61M 2005/2433* (2013.01); *A61M 2005/2485* (2013.01); *A61M 2005/2492* (2013.01)

(58) Field of Classification Search
CPC .... A61M 2205/582; A61M 2005/2451; A61M 2005/2073; A61M 5/2066; A61M 5/24; A61M 5/28; A61M 2005/2403; A61M 2005/2433; A61M 2005/2492; A61M 5/2437; A61M 2005/2411; A61M 2005/2485; A61M 2005/2496; A61M 2005/2407; A61M 2005/2414; A61M 2005/2488; A61M 2005/2437; A61M 5/284; A61M 5/31596; A61M 5/3294; A61M 5/3146; A61M 5/31551; A61M 5/31535; A61M 5/31541; A61M 5/3158

See application file for complete search history.

(56) References Cited

U.S. PATENT DOCUMENTS

| | | | |
|---|---|---|---|
| 8,343,103 B2* | 1/2013 | Moser | A61M 5/2448 604/134 |
| 2005/0049551 A1* | 3/2005 | Kirchhofer | A61M 5/2448 604/82 |
| 2009/0259181 A1 | 10/2009 | Moser | |
| 2009/0275914 A1 | 11/2009 | Harms et al. | |
| 2010/0087799 A1 | 4/2010 | Galbraith et al. | |
| 2012/0035538 A1 | 2/2012 | Elmen et al. | |

OTHER PUBLICATIONS

International Preliminary Report on Patentability in International Application No. PCT/EP2014/069038, dated Mar. 15, 2016, 5 pages.

* cited by examiner

A-A

B-B

C-C

D-D

E-E

DRUG DELIVERY DEVICE

CROSS-REFERENCE TO RELATED APPLICATIONS

This application is a U.S. national stage application under 35 USC § 371 of International Application No. PCT/EP2014/069038, filed on Sep. 8, 2014, which claims priority to European Patent Application No. 13183656.1, filed on Sep. 10, 2013, the entire contents of which are incorporated herein by reference.

TECHNICAL FIELD

The present disclosure relates to a drug delivery device and in particular to an injection device such as a pen-type injector.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. They further comprise a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing or needle assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a dose actually set is entirely injected.

There already exist some drug delivery devices with end of content mechanisms or last dose mechanisms. Most of these mechanisms require a rather complicated interaction of components of a drive mechanism. Typically, a separate last dose limiting member is required that successively propagates either in distal or proximal direction every time a dose is set or dispensed. When reaching an end of content configuration, a last dose limiting member typically engages with a corresponding stop to inhibit a further dose incrementing operation or actuation of the delivery device.

Numerous last dose limiting implementations are non-visibly integrated somewhere in the drive mechanism of such drug delivery or injection devices. A user not being aware that the content of a cartridge is almost used up may be fairly surprised or confused when being suddenly confronted with an end of content situation. In circumstances in which the residual amount of medicament left in a cartridge is smaller than a prescribed dose to be administered the user may be in need of a spare cartridge. However, when being unaware, that such an end of content situation is likely to occur, a new cartridge may be unavailable to the user when the end of content is actually reached.

SUMMARY

In order to avoid such situations, in certain aspects of the present invention provide, a drug delivery device is configured to clearly, unambiguously and intuitively indicate to a user the actual filling level of a cartridge. In some aspects, an improved end of content mechanism is provided without making use of a separate last dose limiting member. In this regard some aspects reduce the number of parts of the drug delivery device.

In a first aspect a drug delivery device for dispensing, in particular for injecting of a dose of a medicament is provided. The drug delivery device, typically designed as an injection device comprises an elongated body extending in an axial direction. Typically, the body is of substantially tubular or cylindrical shape that allows gripping and operating of the device by one hand of a user.

The drug delivery device further comprises a cartridge holder to accommodate and to receive a cartridge that is at least partially filled with the medicament to be dispensed. The cartridge further has an axially displaceable piston, typically serving as a proximally located seal of the cartridge. The piston is displaceable in axial distal direction, thereby inducing a respective pressure in the inside volume of the cartridge in order to expel an amount of the medicament from the cartridge. For such a dispensing action, the distal seal of the cartridge, typically in form of a pierceable septum is in fluid connection with a piercing assembly or needle assembly. Axial displacement of the piston relative to the barrel of the cartridge directly corresponds to the size of a dose and hence correlates to the amount of medicament dispensed therefrom.

The body and the cartridge holder typically form the housing of the drug delivery device and define its outer shape, which may be further completed by a removable protective cap that is typically releasably engageable with a distal portion of the body and which encapsulates the cartridge holder and the cartridge located therein when the device is not in use.

The drug delivery device further comprises a piston rod to operably engage with the piston of the cartridge. By way of the piston rod, distally directed thrust can be exerted to the piston in order to displace the piston in distal direction relative to the cartridge's barrel. Displacement of the piston rod in distal direction exclusively takes place during dose dispensing and is typically controlled and conducted by a drive mechanism of the drug delivery device that is located in the body. The body typically forms a proximal portion of the housing of the drug delivery device while the cartridge holder forms a distal end thereof. Since the drive mechanism is located in the body, the drug delivery device is operable and configurable by a user at its proximal end.

Additionally, the drug delivery device comprises a coupling member connected with the cartridge holder. The coupling member is further axially displaceably arranged in the body for retracting the cartridge holder into the body during setting of a dose. Typically, a coupling member is retractable in proximal direction into the body for retracting the cartridge holder in proximal direction at least during or for a respective dose setting procedure.

During dose dispensing the coupling member is substantially inactive and rests at the position previously occupied at the end of the dose setting procedure. Hence, during dose dispensing the coupling member and also the cartridge holder interconnected therewith are substantially immobile relative to the body. Since coupling member and cartridge holder are subject to proximally directed displacement during dose setting, the overall axial extension of the drug delivery device shortens during and after each successive dose setting procedure.

Moreover, the magnitude of the displacement of the coupling member and hence of the cartridge holder relative to the body in proximal direction is directly correlated to the size of the dose actually set. In this way, the axial displacement of the cartridge holder relative to the body during dose setting is a direct measure and indication of the size of the dose.

Since the cartridge holder and the coupling member do not return into an initial position during a subsequent dose dispensing procedure the cartridge holder is successively retracted into the body until an end of content configuration correlating to a substantially empty cartridge has been reached. It is here of particular benefit that an end of content mechanism can be implemented by a mutual interaction and/or by a relative axial displacement of cartridge holder and housing. In this way, implementation of a separate last dose limiting member is no longer required and the number of components of the drug delivery device can be effectively reduced. Additionally, retraction of the cartridge holder into the body provides a very intuitive and unambiguous approach to visually or even to haptically indicate the filling level of a cartridge to a user. By successively retracting the cartridge holder into the body the overall length of the housing of the drug delivery device is inherently indicative of the cartridge's filling level.

According to an embodiment the cartridge holder is non-rotatably connected to the body and is further radially and axially guided in and by a through opening at the body's distal end. In effect, the cartridge holder and the body are slidingly connected to allow a sliding displacement or a sliding retraction of the cartridge holder into the body. Typically, the inner diameter or inner geometry of the body's through opening matches with the outer circumference of the cartridge holder.

In order to retract the cartridge holder into the body, the cartridge holder comprises an elongated shape, extends in axial direction and features a substantially constant cross-section perpendicular to the axial direction. Radial and axial guidance of the cartridge holder is therefore provided by the through opening located in a distal end face of the body. Additionally and in order to improve axial guiding of the cartridge holder the body may comprise an axially extending shaft portion at the circumference of the through opening. By means of said shaft portion, typically extending in proximal direction, a precise sliding displacement of the cartridge holder relative to the body, substantially free of tilt or cant can be provided.

According to another embodiment body and cartridge holder are keyed engaged in order to prevent mutual rotation of cartridge holder and body with regard to a central axis extending in axial direction. The keyed engagement is typically obtained by at least one pair of mutually corresponding radially extending protrusions and recesses of body and cartridge holder. Hence, the cartridge holder may comprise at least one symmetry breaking protrusion or recess to engage with a correspondingly shaped recess or protrusion of the body, typically provided at the outer circumference of its through opening.

In another embodiment the body comprises at least one radially inwardly extending protrusion extending into an axially extending through opening of the cartridge holder. Instead of a through opening the cartridge holder may comprise a recess at its outer circumference that does not completely penetrate the cartridge holder's sidewall portion. The axially extending through opening of the cartridge holder is typically provided in a sidewall portion of the substantially tubular-shaped cartridge holder.

The through opening may further serve as an inspection window providing visual access to the cartridge arranged in the cartridge holder. By way of the through opening, the content of the cartridge may be visually inspected by the user. Typically, the circumferential size of the body's protrusion and of the cartridge holder's through opening mutually match so that protrusion and through opening effectively inhibit mutual rotation of cartridge holder and body.

In typical embodiments the body comprises two diametrically positioned radially inwardly extending protrusions mating with two diametrically oppositely located through openings of the cartridge holder. By providing two or even more pairs of inter-engaging protrusions and through openings of body and cartridge holder a multiple rotational interlock of cartridge holder and body can be provided that may support a smooth sliding displacement of cartridge holder and body.

Moreover, when having several pairs of mutually engaged protrusions and through openings or recesses, forces or torque acting between cartridge holder and body in circumferential direction may be evenly distributed among the pairs of inter-engaging protrusions and through openings.

According to an alternative embodiment it is the cartridge holder featuring a radially outwardly extending protrusion engaged and guided in a correspondingly shaped axially extending recess or through opening of the body.

According to another embodiment, the through opening of the cartridge holder or a correspondingly acting recess thereof comprises a stop edge at its distal end to delimit a proximally directed displacement of the cartridge holder relative to the body when reaching an end of content configuration. Typically, the through opening or recess of the cartridge holder terminates at the distal stop edge. In this way, the stop edge inherently provides a stop face to abut with the body's protrusion when reaching an end of content configuration of the cartridge.

When the radially inwardly extending protrusion of the body abuts with said stop edge of the cartridge holder, the cartridge holder cannot be displaced any further in proximal direction relative to the body. Since the proximally directed displacement of the cartridge holder is directly coupled to a dose setting, a respective dose setting procedure is delimited and stopped. In this way, the mutual interaction, in particular the mutual axial abutment of the body's protrusion and the cartridge holder's stop edge effectively provides an end of content mechanism.

According to another embodiment the drug delivery device, in particular its drive mechanism comprises drive sleeve rotatably supported in the body and being operably engageable with the piston rod to induce a distally directed displacement of the piston rod for dispensing of a dose. Moreover, the drive sleeve may not only be operable for dose dispensing but also for dose setting. The drive sleeve may rotate in a dose incrementing direction during dose setting. It may rotate in the opposite direction, hence in a dose decrementing direction during dispensing of a dose.

Typically, for dispensing of a dose the drive sleeve is operably connectable to the piston rod in order to drive the piston rod in distal direction. During dose setting, the drive sleeve may be effectively disengaged from the piston rod. The drive sleeve may further be engaged with a spring element, typically with a helically-shaped spring element that is configured to transfer a driving torque to the drive sleeve during a dose dispensing procedure. The spring element may either be selectively or permanently coupled to the drive sleeve. When permanently coupled to the drive sleeve the spring element may be strained or biased during a dose setting procedure when the drive sleeve is rotated in dose incrementing direction. By some kind of clutch or ratchet mechanism the energy transferred to the spring element may then be stored and saved in or by said spring element until a dose dispensing action is triggered during which the energy stored in the spring element is to be released to exert a driving torque to the drive sleeve, i.e. to induce a rotation of the drive sleeve in dose decrementing direction.

In another embodiment, wherein the drive sleeve is only selectively coupled or engaged with the spring element, the spring element may be pre-tensioned in such a way, that the energy or torque stored in the spring element is sufficient for subsequent dispensing procedures. In particular, the spring element may be charged or biased for the entire lifetime of a respective drug delivery device.

According to another embodiment the piston rod is displaceable in proximal direction relative to the body and/or relative to the drive sleeve for setting of the dose. Here, the piston rod may be in permanent contact with the piston of the cartridge. Since the cartridge holder and the cartridge located therein is retracted in proximal direction relative to the body during setting of a dose, the same may also be valid for the piston rod. In a subsequent dose dispensing procedure cartridge holder and the cartridge located therein are immobilized relative to the body while the piston rod is driven in distal direction relative to the body and hence relative to the cartridge holder and relative to the cartridge.

Typically, the piston rod is subject to proximally and distally directed displacement relative to the body during dose setting and dose dispensing, respectively. Typically, the magnitude or distance of a proximally directed displacement during dose setting is substantially equal to a subsequent distally directed displacement of the piston rod during dose dispensing. Hence, at the end of a dose dispensing procedure the piston rod returns into an initial configuration relative to the body.

Drive sleeve and piston rod are mutually engaged by some kind of clutch mechanism that allows proximally directed displacement of the piston rod relative to the drive sleeve when the device is in dose setting mode. However, in dose dispensing mode drive sleeve and piston rod are mutually engaged in such a way, that a rotation of the drive sleeve transfers into a distally directed displacement of the piston rod.

According to another embodiment the drug delivery device further comprises a sleeve-shaped retraction member rotatably supported in the body and being threadedly engaged with the coupling member. The retraction member is typically axially constrained or axially fixed in the housing and may therefore only rotate relative to the housing, at least during dose setting or for dose setting. Moreover, the coupling member and the cartridge holder are typically non-rotatably connected.

Additionally, coupling member and cartridge holder are typically axially and rotatably fixed relative to each other. Since the cartridge holder is further non-rotatably connected to the body also the coupling member is non-rotatable relative to the body. Since the retraction member and the coupling member are threadedly engaged, a rotation of the retraction member relative to the housing therefore leads to an axial displacement of the coupling member relative to the housing, thereby retracting the cartridge holder into said housing.

Typically, the retraction member is rotatable only during dose setting but is decoupled from the drive mechanism during dose dispensing. It is of particular benefit here, when the retraction member is rotatably locked to the housing in order to impede and to block any axial displacement of the cartridge holder relative to the body during dose dispensing. During dose setting, the retraction member is rotatable in both directions, i.e. in dose incrementing direction for increasing of a dose size as well as in dose decrementing direction for decreasing or for correcting a dose previously set.

When the retraction member rotates in a dose incrementing direction the coupling member is displaced in proximal direction relative to the housing and/or relative to the retraction member. In the opposite case, when the retraction member rotates in a dose decrementing direction, the coupling member is subject to a corresponding distally directed axial displacement relative to the housing and/or relative to the retraction member.

According to another embodiment, the drive sleeve and the retraction member are rotatably coupled for dose setting. Moreover, for dose dispensing the drive sleeve and the retraction member are rotatably disengaged. In this way, the retraction member is rotatable by means of the drive sleeve when the drug delivery device is in dose setting mode whereas the retraction member is substantially inactive or even immobilized relative to the body when the device is in dose dispensing mode.

Typically, the drive sleeve is at least partially inserted into the hollow retraction member. Here, the drive sleeve typically comprises an outer geared rim or an outer toothing engaged with a correspondingly shaped toothing provided on an inwardly facing sidewall portion of the retraction member. In this way, a torque acting on the drive sleeve during dose setting can be unalterably transferred to the retraction member. For dose dispensing the mutually corresponding toothings of drive sleeve and retraction member are disengaged, e.g. by an axial displacement of the drive sleeve relative to the retraction member.

Typically, the drive sleeve is engaged with a proximal end of the retraction member while a distal end section of the retraction member is threadedly engaged with the coupling member. The hollow and sleeve-shaped retraction member comprises an inner thread and an inside-facing tubular sidewall portion. In this way, the coupling member having an outer thread to threadedly engage with said inner thread of the retraction member is initially located near a distal end of the retraction member.

During successive dose setting procedures the coupling member is therefore displaced in proximal direction, thereby retracting the cartridge holder into the hollow retraction member. Consequently, the retraction member is adapted to almost completely receive the cartridge holder, typically, until the stop edge of the cartridge holder provided at a distal end thereof engages with the radially inwardly extending protrusion of the body, which is typically located at the body's distal end. In said end of content configuration cartridge holder and body are arranged in an interleaved, hence in an axially and/or radially overlapping configuration.

According to another embodiment the drive sleeve is rotatably engageable with a drive member threadedly engaged with the piston rod. Drive member and drive sleeve may be permanently rotatably engaged or rotatably coupled. Alternatively, drive member and drive sleeve may be selectively rotatably engaged or rotatably coupled or selectively rotatably connected. The drive member typically comprises or forms a drive nut rotatably or threadedly supported on the outer circumference of the piston rod. The drive member comprises an inner thread that corresponds and mates with an outer thread of the piston rod. Typically, the drive member is axially secured or axially constrained in the housing. The drive member may be for instance axially coupled with the drive sleeve. Since the drive member is either axially immobilized or axially constrained, rotation of the drive member then leads to an axial displacement of the piston rod, given that the piston rod is rotatably fixed relative to the body.

The threaded engagement of drive member and piston rod may be of non-self-locking type, i.e. an axial displacement of the piston rod, in particular a proximally directed axial displacement of the piston rod, may then transfer into or induce a rotation of the drive member, which is axially fixed in the housing. This type of threaded engagement between piston rod and drive member would allow and support a selective rotational engagement of drive member and drive sleeve. Especially during setting of a dose, which is accompanied by a proximally directed displacement of the piston rod relative to the housing, the drive member could rotate independent from the drive sleeve. In other embodiments it is conceivable that the drive member and the drive sleeve are permanently rotatably engaged. During setting of a dose the drive member would then rotate in unison with the drive sleeve.

In particular, the drive sleeve is rotatably engageable with the drive member in order to transfer a driving torque to the drive member. Due to the threaded engagement of drive member and piston rod and due to the axial coupling of the drive member relative to the body the piston rod, when rotatably locked to the body, experiences a distally directed displacement as the drive member is rotated in a dose decrementing direction by means of a correspondingly rotating drive sleeve.

Typically, drive sleeve and drive member are rotatably engaged at least only during dose dispensing or only during dose dispensing. During dose setting drive sleeve and drive member may be operably disengaged. Drive sleeve and drive member may provide a kind of a clutch mechanism, by way of which the drive sleeve can be selectively engaged and coupled with the piston rod. By operably disengaging drive sleeve and drive member during dose setting, the drive sleeve can be rotated for setting of a dose without any interaction with the piston rod. In this way, the piston rod remains completely unaffected by a rotation of the drive sleeve for dose setting purpose.

According to another embodiment the piston rod axially extends through a coupling member's through opening. Typically, piston rod and coupling member are keyed engaged. Hence, the piston rod is non-rotatably coupled to the coupling member. For this, the piston rod typically comprises a longitudinal groove engaging with a radially inwardly extending pin or a respective protrusion pointing radially inwardly from the inner circumference of the coupling member's through opening. In this way, the piston rod is axially but non-rotatably guided in or by the coupling member.

Moreover, since the piston rod is rotatably locked to the coupling member and since the coupling member is rotatably locked to the cartridge holder, which in turn is rotatably locked to the body, the piston rod cannot rotate relative to the body. Since the piston rod is further threadedly engaged with the drive member, a rotation of the drive member transfers to an axial displacement of the piston rod relative to the body and hence relative to the cartridge holder and relative to the cartridge arranged therein.

In still another embodiment the drug delivery device further comprises a single dose limiting member threadedly engaged with the piston rod and being non-rotatably but axially displaceably engaged with the drive sleeve. By means of the dose limiting member axial displacement of the piston rod can be delimited or restricted in at least one axial direction. Typically, the dose limiting member provides at least a zero dose stop by way of which a distally direction displacement of the piston rod can be stopped when the piston rod approaches an initial configuration at the end of a dose dispensing procedure.

The single dose limiting member typically comprises a dose limiting disc or a respective dose limiting nut non-rotatably engaged, hence rotatably locked with the drive sleeve. For this, the dose limiting member comprises a radially extending protrusion or a radial recess at its outer circumference to mate with a correspondingly shaped recess or protrusion at an inward facing sidewall portion of the drive sleeve.

The single dose limiting member may axially abut with a proximal end face of the drive member. Furthermore, the dose limiting member may comprise a radial or axial stop to engage with a correspondingly, typically radially outwardly extending radial or axial stop provided on the outer circumference of the piston rod. When the mutually corresponding stops of the single dose limiting member and the piston rod get in direct abutment, a rotation of the dose limiting member relative to the piston rod can be blocked. Such a blocking typically coincides with a zero dose configuration. By means of this zero dose stop function it can be effectively prevented, that a negative dose is set, e.g. by turning or twisting a respective dose setting member in a wrong direction for setting of a dose.

The drug delivery device further comprises a maximum dose limiting feature. This may be implemented by a mutual interaction of the piston rod and the drive member. For instance, the piston rod comprises a second radially outwardly extending radial or axial stop element to engage with a correspondingly shaped stop of the drive member. The respective stop of the drive member may be located at a distal end face thereof. Typically, when implemented as a drug delivery device for injecting insulin, a stop configuration of the second or distal stop of the piston rod with the distal end face of the drive member serves to limit the maximum size of a dose to e.g. 120 international units (IU) of insulin.

According to another embodiment the threaded engagement of the coupling member and the retraction member and the threaded engagement of the piston rod and the drive member comprise an equal pitch. Moreover, also the threaded engagement of the piston rod and the single dose limiting member and the threaded engagement of the piston rod and the drive member may comprise an equal pitch. Additionally or alternatively also the threaded engagement of the piston rod and the single dose limiting member and the threaded engagement of the coupling member and the retraction member comprise a substantially equal pitch.

In this way axial displacement of the coupling member relative to the retraction member is substantially the same as the axial displacement of the piston rod relative to the drive member and relative to the single dose limiting member during setting of a dose, i.e., when the retraction member is subject to a dose incrementing or dose decrementing rotation.

Since the piston rod is threadedly engaged with the drive member and since the drive member is axially constrained or even axially fixed relative to the body and/or relative to the drive sleeve it is of particular benefit, when the drive member rotates in unison with the drive sleeve during dose setting. In this way the piston rod can be displaced in proximal direction relative to the drive member and relative to the drive sleeve in the same way as the cartridge holder is retracted into the body.

According to another embodiment the drug delivery device further comprises a blocking member engaged with a pretensioned spring element. The blocking member is further alternately engageable with the body or with the drive sleeve. Typically, the blocking member is engaged with the body and is disengaged from the drive sleeve during dose setting. In this way, the drive sleeve can be rotated for dose setting purpose without any interaction with the spring element. It is only due to dose dispensing, that the blocking member is disengaged from the body and is simultaneously engaged with the drive sleeve.

In this way, mechanical energy stored and provided by the spring element can be released in order to exert a driving torque to the drive sleeve, e.g. to trigger and to conduct a spring-biased dose dispensing procedure.

By selectively or alternately engaging the blocking member either with the body or with the drive sleeve a pretensioned spring element can be used that is operable to store such an amount of mechanical energy that is sufficient for completely dispensing the entire content of the cartridge during subsequent dose dispensing procedures. Especially when implemented as a disposable drug delivery device, a spring element being 'charged for life', hence for the entire life cycle of the device, can be applied here.

According to another embodiment the drive sleeve is axially displaceable between a proximal stop position and a distal stop position for switching between a dose setting mode and a dose dispensing mode. Displacement of the drive sleeve in distal direction is such, that the drive sleeve rotatably engages with the blocking member and further disengages the blocking member from the body. At the same time the axial displacement of the drive sleeve, e.g. in distal direction serves to disengage the drive sleeve from the retraction member. Moreover, by means of a distally directed displacement of the drive sleeve from its proximal stop position into its distal stop position the drive sleeve may rotatably engage or may rotatably interlock with the drive member for transferring a driving torque from the relaxing spring element via the blocking member to the drive sleeve, to the drive member and hence to the piston rod for driving the same in distal direction.

Axial displacement of the drive sleeve therefore fulfils three functions. First of all, the blocking member can be selectively engaged and disengaged to and from the body. Second, the drive sleeve could be rotatably engaged and disengaged with the drive member and third, the drive sleeve can selectively engage and disengage with or from the retraction member. In this way, three different clutch mechanisms are integrated or realized by a single element of the drug delivery device or of its drive mechanism, namely by the drive sleeve.

Distally directed displacement of the drive sleeve may act against a retraction spring, which may either be integrated or engaged with the drive sleeve itself or with a clutch element axially fixed to the drive sleeve and being further supported by the body.

In still another embodiment the drug delivery device further comprises a cartridge that is at least partially filled with the medicament to be dispensed. Said cartridge is arranged in the cartridge holder and is displaceable relative to the body together with the cartridge holder. Here, it is particularly due to the axial abutment of the piston of the cartridge with the piston rod, that the piston rod experiences a proximally directed displacement relative to the drive member and/or relative to the drive sleeve during setting of a dose, i.e. when the cartridge holder together with the cartridge disposed therein is retracted in proximal direction relative to the body.

The drug delivery device may be designed as a disposable drug delivery device which is intended to be completely discarded upon consumption of the medicament initially provided in the cartridge. Alternatively, the drug delivery device may be designed as a reusable device, wherein the cartridge holder is releasably connected to the coupling member. Additionally, there may be implemented a reset function, to return the piston rod into an initial configuration upon replacement of a cartridge.

By means of the pretensioned spring element the user does not have to provide a driving force to induce a driving torque on the drive sleeve. Instead, the user may only have to axially displace the drive sleeve from its proximal dose setting position into its distal dose dispensing position. The mechanical energy or torque necessary to displace the piston rod in distal direction for expelling of a predefined amount of the medicament from the cartridge may be completely provided by the pretensioned spring element.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, a brief description of the drawings is provided, in which.

DETAILED DESCRIPTION

Figure 1:
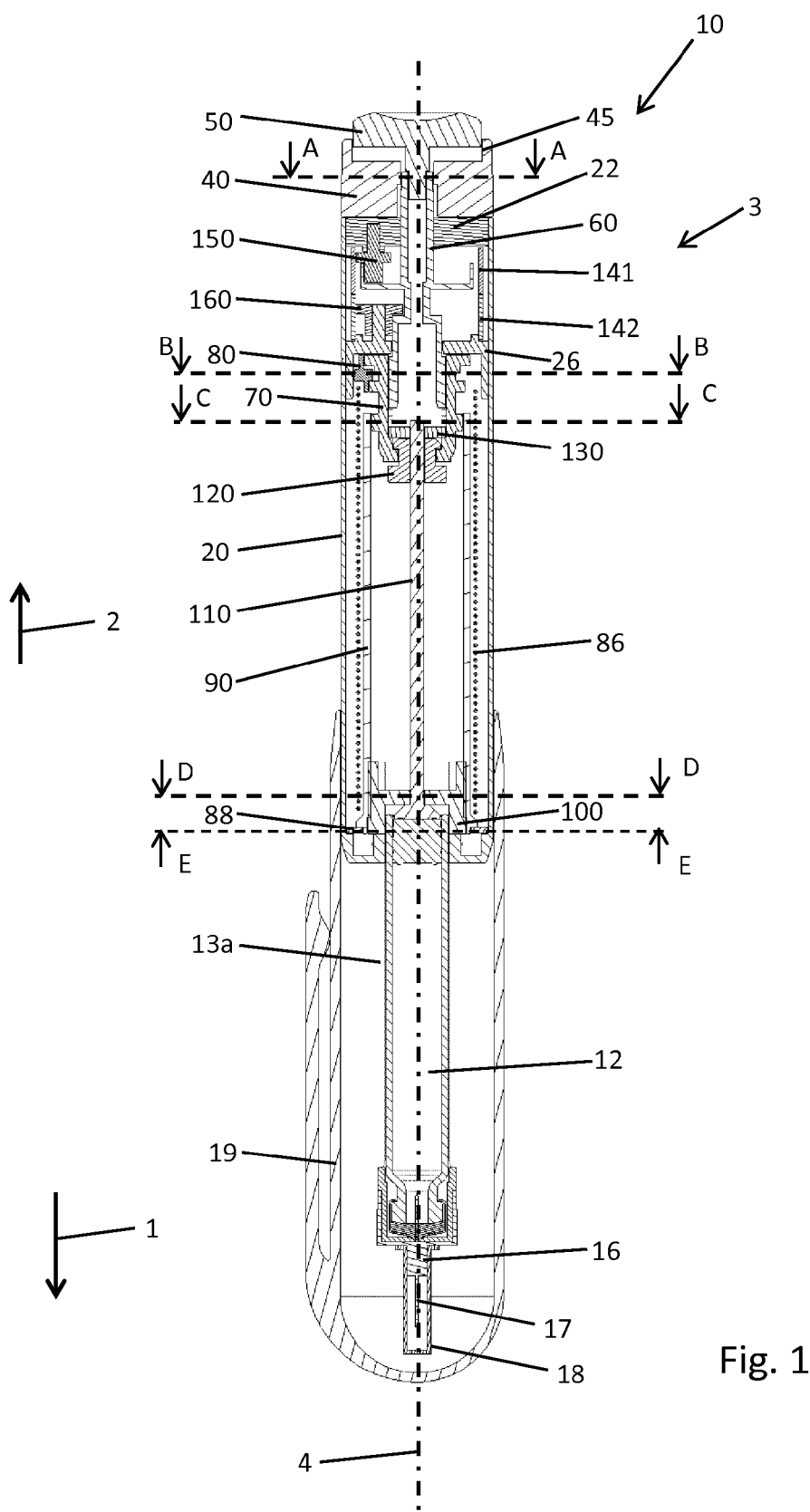
FIG. 1 schematically illustrates the drug delivery device in a longitudinal cut.
Figure 9:
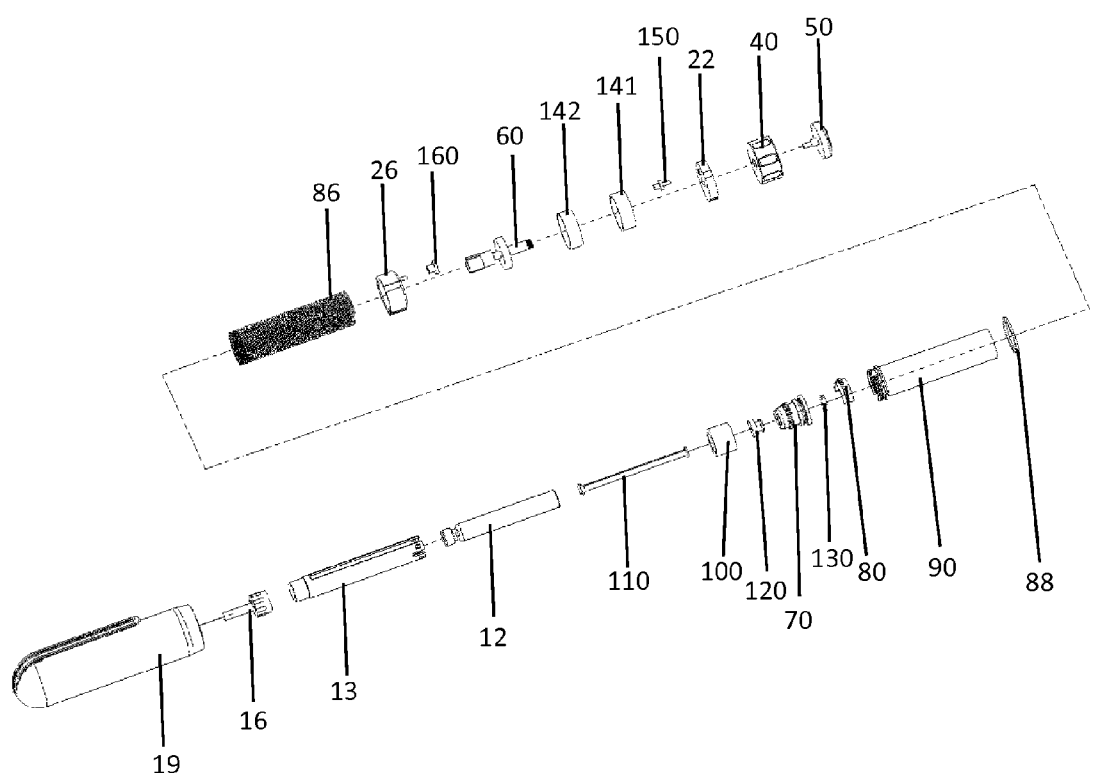
FIG. 9 shows an exploded view of the various components of the drug delivery device, without the body
Figure 10:
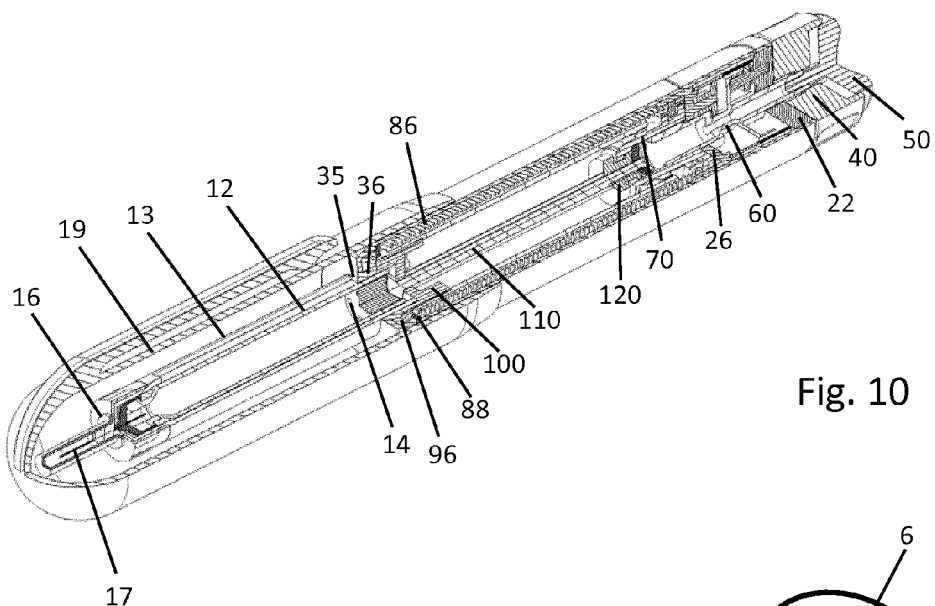
FIG. 10 shows a perspective and partially cut view through the assembled drug delivery device.

In FIGS. 1, 9 and 10, the complete drug delivery device 10 is illustrated in a longitudinal cross-section and in an exploded view. The drug delivery device 10 of pen-injector type comprises a substantially cylindrical and axially elongated shape. The device 10 comprises a central axis 4 extending in axial direction. Throughout the various Figures, the axial distal direction is denoted with reference number 1 and the opposite proximal direction is denoted with reference number 2.

The drug delivery device 10 comprises a body 20 and a cartridge holder 13. Body 20 and cartridge holder 13 form a housing of the drug delivery device 10, which may be completed by a protective cap 19 that is releasably engageable with a distal end portion of the body 20 and which is adapted to completely cover the cartridge holder 13 and a cartridge 12 disposed therein.

The drug delivery device 10 further comprises a drive mechanism 3 featuring at least a piston rod 110 that is operably engageable with a piston 14 of the cartridge 12. The drive mechanism 3 is operable to displace the piston rod 110 in distal direction 1 in order to displace the piston 14 relative to the cartridge 12 accordingly for dispensing of a dose of the liquid medicament contained in said cartridge 12. The cartridge 12 typically comprises a vitreous barrel of cylindrical or tubular shape and is further sealed at its distal end by a pierceable sealing member, such like a septum.

Figure 16:
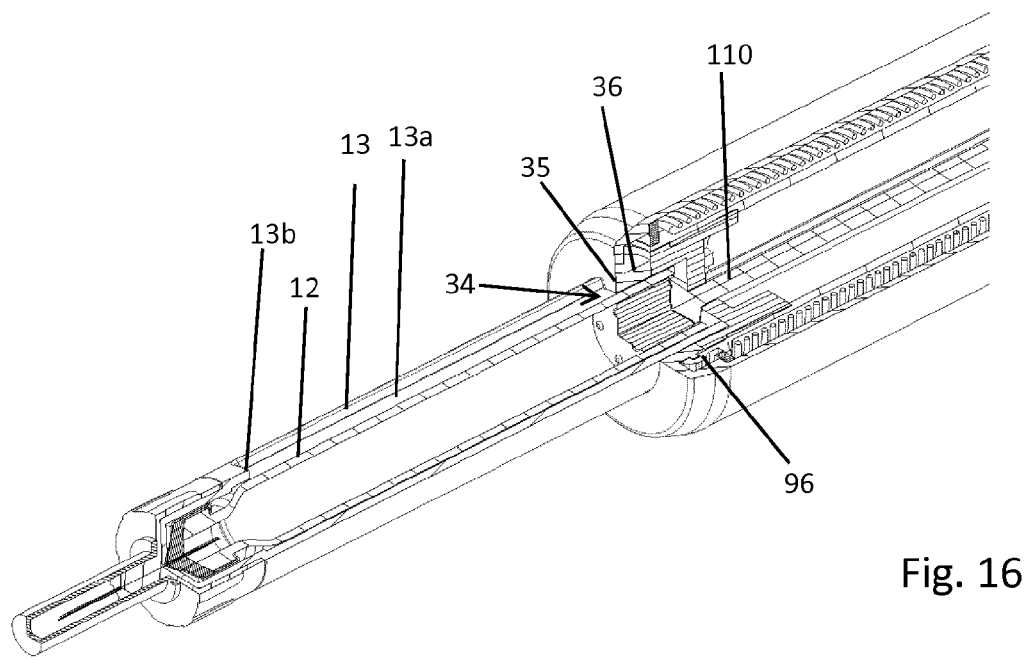
FIG. 16 shows a partially cut and perspective illustration of the interface of cartridge holder and body in an initial configuration and FIG. 17 shows the interface of cartridge holder and body in an end of content configuration.
Figure 17:
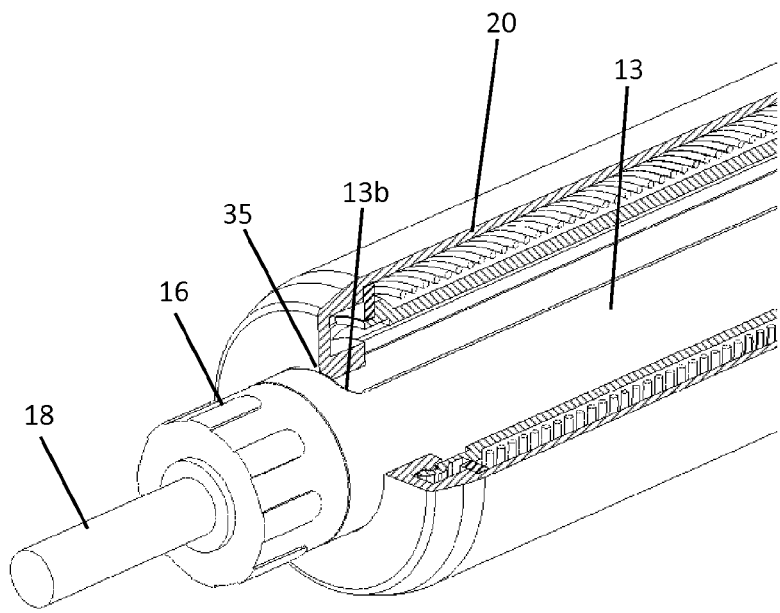

In proximal direction 2 or at its proximal end, the cartridge 12 is sealed by means of the piston 14 slidably arranged in the cartridge 12. The piston 14 typically comprises an elastomeric material, by way of which the proximal end of the cartridge is effectively sealed in a fluid- and gas-tight manner. Distally-directed displacement of the piston 14 induced by a respective displacement of the piston rod 110 typically leads to the build up of a fluid pressure inside the cartridge 12. The distal outlet of the cartridge 12 is typically connected with a piercing member or with a needle assembly 16 as illustrated in FIGS. 1, 16 and 17. Since the needle assembly 16 comprises a double-tipped injection needle 17, a dose of the medicament can be expelled from the cartridge 12 through the needle assembly 16 and can be injected into biological tissue. Typically, as illustrated in FIGS. 1, 16 and 17, the injection needle 17 is covered by an inner needle cap 18 that is to be removed prior to an injection procedure.

The needle assembly 16 is typically removably attached to the distal end portion of the cartridge holder 13. Here, a distally-located socket of the cartridge holder 13 and the needle assembly 16 may comprise mutually corresponding threads to screw the needle assembly 16 onto the cartridge holder 13 in a releasable way.

Prior to conduct an injection procedure, the protective cap 19 has to be removed while the needle assembly 16 has to be attached to the cartridge holder 13. After completion of a dose dispensing or injection procedure, the needle assembly 16 is to be removed and to be discarded and the protective cap 19 is to be assembled to the body 20 for protecting and for receiving the cartridge holder 13.

The drive mechanism 3 as illustrated in the various FIGS. 1-19 comprises numerous functional and mechanically interengaging components by way of which a dose of variable size can be set and subsequently dispensed. The drive mechanism 3 is of semi-automated type. It comprises a means for storing mechanical energy either during a dose setting procedure or it is even equipped with an energy storage means, such like a pretensioned helical spring element 86 that is charged or biased in such a way, that it does not have to be biased or strained any further during dose setting. In particular with a disposable drug delivery device the spring element may be initially 'charged for life'.

The mechanical energy stored and provided by the helical spring element 86 is exploited for driving the piston rod 110 in distal direction 1 during a dose dispensing procedure. Consequently, an injection force or injection torque does not have to be provided by a user of the device 10 during the dose dispensing process.

The body 20 comprises a tubular or cylindrical shape and features a window 21 near its proximal end, where a display assembly 140 is arranged. Near its distal end or in its distal end face the body 20 comprises a through opening 34 to receive the outer circumference of the tubular-shaped cartridge holder 13. Adjacent to said central through opening 34 there is located a proximally extending shaft portion 36 as illustrated in FIG. 16. Additionally, the through opening 34 features a radially inwardly extending protrusion 35 that mates and engages with a correspondingly shaped through opening 13a of the cartridge holder 13. The through opening 13a serves as an inspection window in order to visually inspect the medicament provided in the transparent cartridge 12.

By means of the radially inwardly extending protrusion 35 of the body 20 engaging with the correspondingly shaped recessed portion or through opening 13a of the cartridge 13, a rotational interlock of cartridge holder 13 and body 20 is provided. In this way, the cartridge holder 13 is translationally displaceable relative to the body 20, e.g. in proximal direction 2 until the radially inwardly extending protrusion 35 of the body 20 axially abuts with a distal stop edge 13b at the distal end of the through opening 13a as indicated in the respective end of content configuration of FIG. 17.

As will be explained below, the cartridge holder 13 is retracted in proximal direction 2 into the body 20 during a dose setting procedure while it remains in the retracted position during a subsequent dose dispensing. The radially inwardly extending protrusion 35 of the body 20 and the correspondingly shaped longitudinal or slit-like through opening 13a of the cartridge holder 13 provide two functions. First of all, the cartridge holder 13 is rotatably interlocked to the body 20 and second, a rather simple but robust and intuitive end of content mechanism can be provided.

As the content, hence the medicament provided in the cartridge reduces in the course of subsequent dispensing procedures the overall axial extension of the drug delivery device 10 reduces as well. Moreover, the axial distance the cartridge holder 13 is retracted into the body 20 during a dose setting procedure is directly related or equivalent to the size of the dose actually set. In this way, the actual dose size but also the total amount of medicament left in the cartridge is directly discernible from the axial position of the cartridge holder 13 in relation to the body 20.

The tubular-shaped body 20 further serves as a mount for a proximal base member 22 located at a proximal end of the body 20. The proximal base member 22 serves as a mount for a first wheel 150 of the display assembly 140. Furthermore, the proximal base member 22 features a central bore to receive and to axially and to radially guide a proximal shaft portion 61 of a clutch member 60.

Additionally, there is also provided a distal base member 26 axially separated from the proximal base member 22. The distal base member 26 serves as a mount for a second wheel 160 of the display assembly 140. Additionally, also the distal base member 26 comprises a central through opening 32 to axially and/or to radially guide a distal shaft portion 65 of the clutch member 60.

Both, the proximal as well as the distal base members 22, 26 are permanently fixed to the body 20. They may even be integrally formed with the body 20. As illustrated in cross-section according to FIG. 3, the distal base member 26 comprises radially inwardly extending recesses 30 to receive correspondingly shaped radially inwardly extending protrusions 24 located at the inward-facing sidewall portion of the body 20.

The proximal base member 22 may be permanently and rigidly attached to the body 20 in a similar way, which is not particularly illustrated here.

Figure 6:
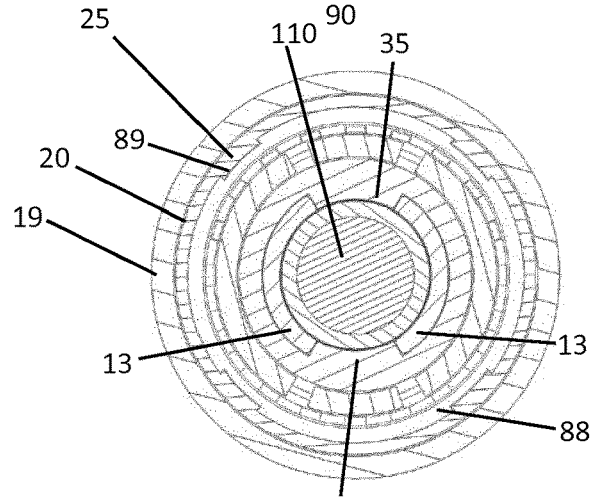
FIG. 6 shows another cross-section E-E according to FIG. 1.
Figure 12:
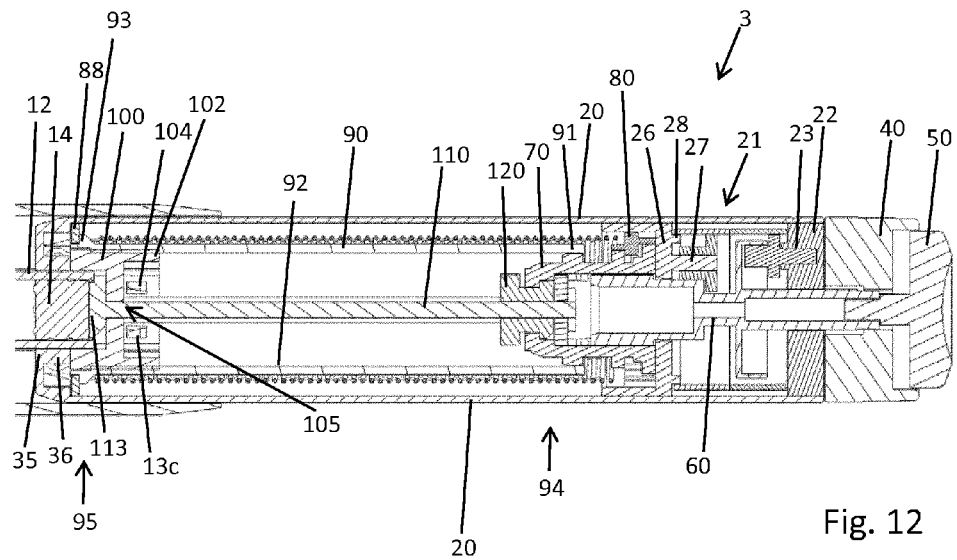
FIG. 12 shows a longitudinal cross-section through the drive mechanism of the drug delivery device in an initial configuration.
Figure 13:
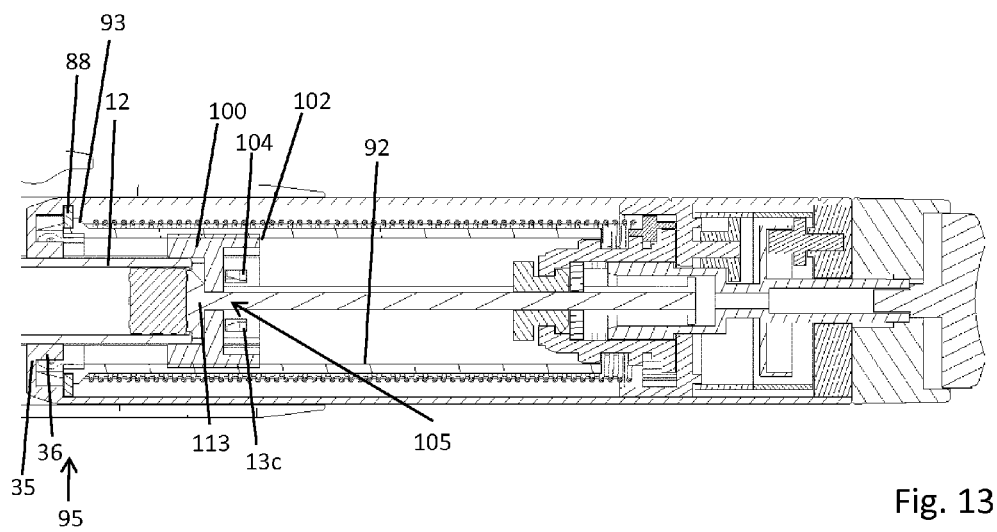
FIG. 13 is indicative of the device according to FIG. 12 after setting of a dose.

The body 20 further serves as a mount for an annular fixing element 88 as illustrated in the cross-section of FIG. 6. The fixing element 88 comprises numerous radially inwardly extending recesses 89 at its outer circumference to engage with correspondingly shaped and radially inwardly extending protrusions 25 of the body 20. By means of mutually corresponding protrusions 25 and recesses 89, the fixing element 88 can be clamped or otherwise fixed inside the body 20. As illustrated in FIGS. 12 and 13, the fixing element 88 is positioned near the distal end of the body 20.

Figure 3:
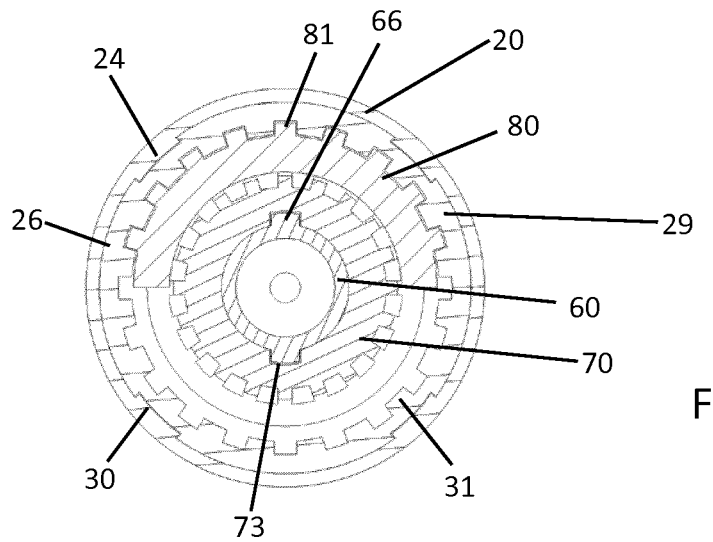
FIG. 3 shows a cross-section B-B according to FIG. 1.
Figure 4:
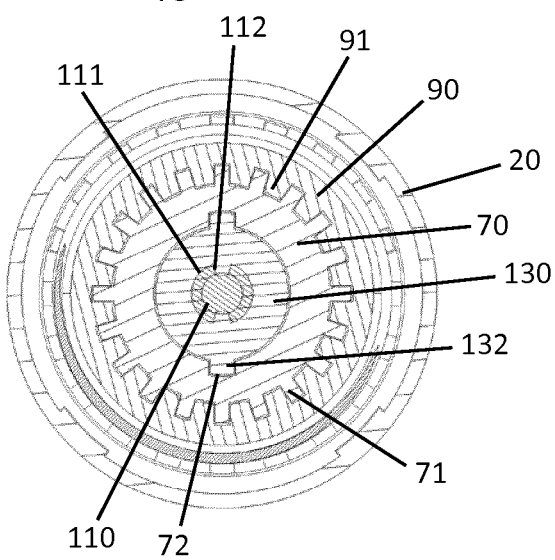
FIG. 4 shows a cross-section along C-C of FIG. 1.

The fixing element 88 further serves as a mount for the helical spring element 86, that winds or extends along the outer circumference of a tubular or sleeve-shaped retraction member 90. The opposite, hence the proximal end of said helical spring element 86 is connected with a blocking member 80, which is of arched shape as indicated in FIGS. 3 and 9 and which is adapted to alternately engage either with the body 20, in particular via the distal base member 26, or with a drive sleeve 70 as becomes apparent from a comparison of FIGS. 18 and 19.

Figure 8:
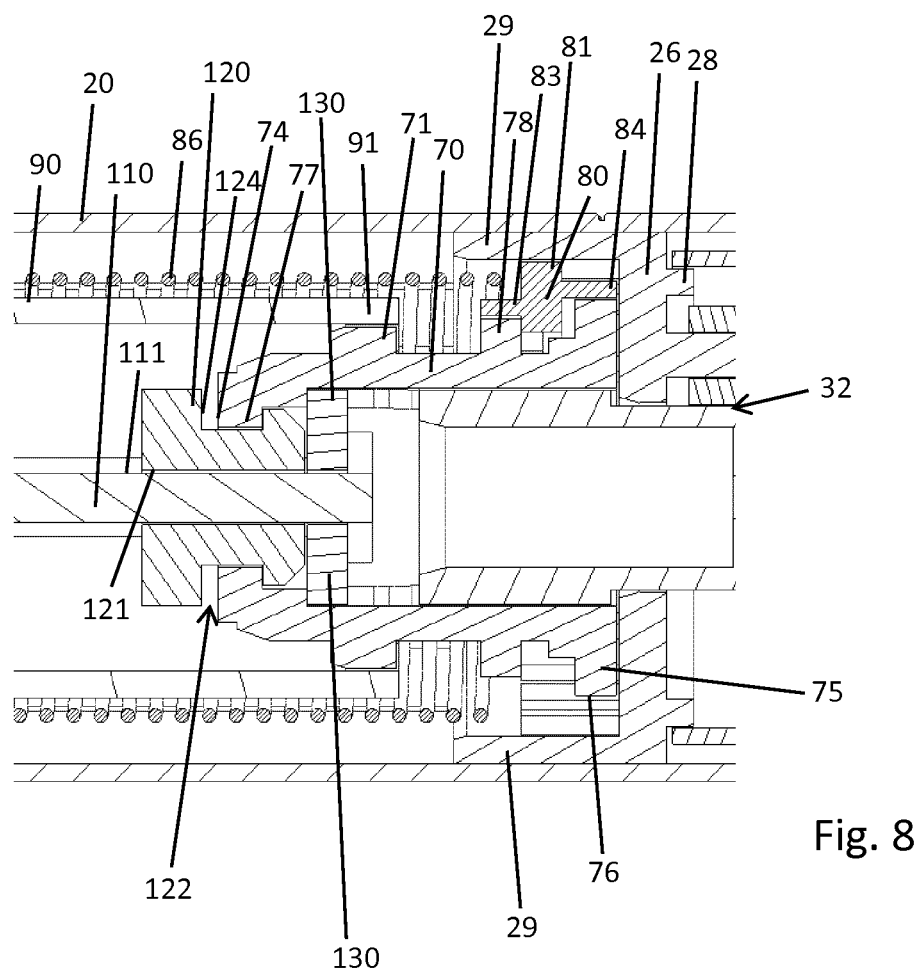
FIG. 8 shows a longitudinal cross-section through the drive sleeve.

The distal base member 26 as for instance illustrated in FIG. 8 comprises a central through opening 32 to axially and radially guide the distal shaft portion 65 of the clutch member 60. Said through opening 32 is provided in a flange-like portion of the distal base member 26 that extends across the cross-section of the body 20. At the outer circumference of said flange portion the distal base member 26 features a sleeve portion 29 substantially extending along the inward-facing side wall of the body 20. By means of the sleeve portion 29, a tight fitting or clamping-like engagement between body 20 and distal base member 26 can be attained.

The retraction member 90 as for instance indicated in FIGS. 12 and 13 is axially fixed to the body 20 by means of a fastening portion 96 located at a distal end thereof. As indicated in FIG. 16, the snap-shaped fastening portion 96 engages with a circumferential and outwardly extending rim located on the shaft portion 36 of the body 20. In this way, the retraction member 90 is free to rotate with respect to the body 20.

Additionally, the retraction member 90 features a radially outwardly extending abutment portion 93 at its distal end 95. This abutment portion 93 axially engages with the fixing element 88 to axially and/or to radially fix the fixing element 88 to the body 20. As indicated in FIG. 12, the fixing element 88 is axially constricted or axially clamped between a radially stepped portion of the body 20 and the abutment portion 93 of the retraction member 90.

Moreover, the retraction member 90 comprises an inner thread 92 by way of which it is threadedly engaged with a coupling member 100 featuring a corresponding outer thread 102 at its outer circumference. The retraction member 90 further comprises a toothing 91 or a geared structure at its proximal end 94 at an inward-facing portion of its tubular sidewall. Said toothing 91 is selectively engageable with a correspondingly shaped distal toothing 71 of the drive sleeve 70. In this way, the drive sleeve 70 and the retraction member 90 are rotatably engaged so that a rotation of the drive sleeve 70 equally transfers into a respective rotation of the retraction member 90.

Figure 5:
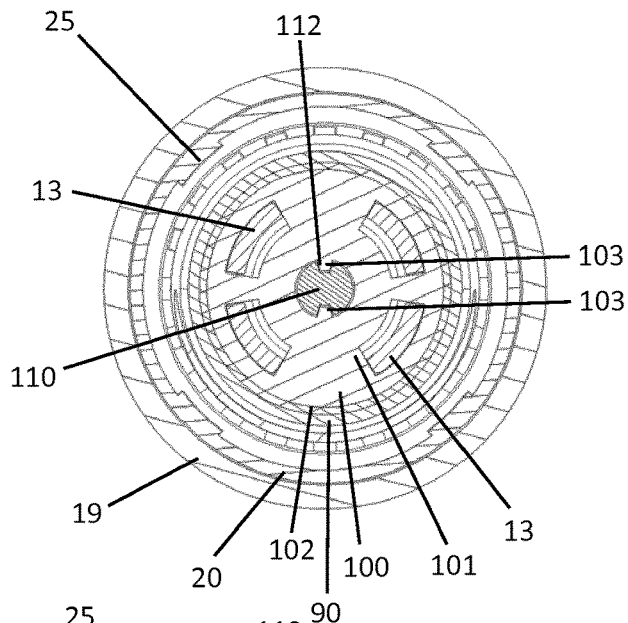
FIG. 5 shows a cross-section along D-D of FIG. 1.

The coupling member 100 as illustrated in cross-section according to FIG. 5 features a flange portion 101 extending substantially perpendicular to the central axis 4. The coupling member 100, in particular its flange portion 101, comprises a central through opening 105 to receive the piston rod 110 extending there through. The through opening 105 comprises two diametrically oppositely-located and radially inwardly extending protrusions 103 engaging with a correspondingly shaped notch or groove 112 of the piston rod 110. Additionally, the coupling member 100 is fixed to the cartridge holder 13. The coupling member 100 comprises a distally and/or proximally extending connecting portion 104 to receive a proximal end of the cartridge holder 13 as illustrated in FIG. 13. Hence, the proximal end of the cartridge holder 13 and the sleeve-like shaped coupling member 100 are arranged in an overlapping or nested configuration.

As becomes apparent from FIGS. 12 and 13, the cartridge holder 13 comprises two or even more through openings 13c at its proximal end to receive radially inwardly extending connecting portions 104 of the coupling member 100. The connecting portions 104 may comprise radially inwardly biased snap elements by way of which the coupling member 100 and the cartridge holder 13 can be mutually engaged in a non-rotative way. Moreover, coupling member 100 and cartridge holder 13 are also axially engaged, so that any axial displacement of the coupling member 100, e.g. inside the retraction member 90 is directly transferred into a corresponding displacement of the cartridge holder 13.

Additionally, since the cartridge holder 13 is rotatably locked to the body 20 and since the cartridge holder 13 is also rotatably locked to the coupling member 100, the coupling member 100 is hindered from rotating relative to the body 20. Consequently, a rotation of the retraction member 90 leads to an axial displacement of the coupling member 100 and hence of the cartridge holder 13 due to the threaded engagement of coupling member 100 and retraction member 90.

Figure 14:
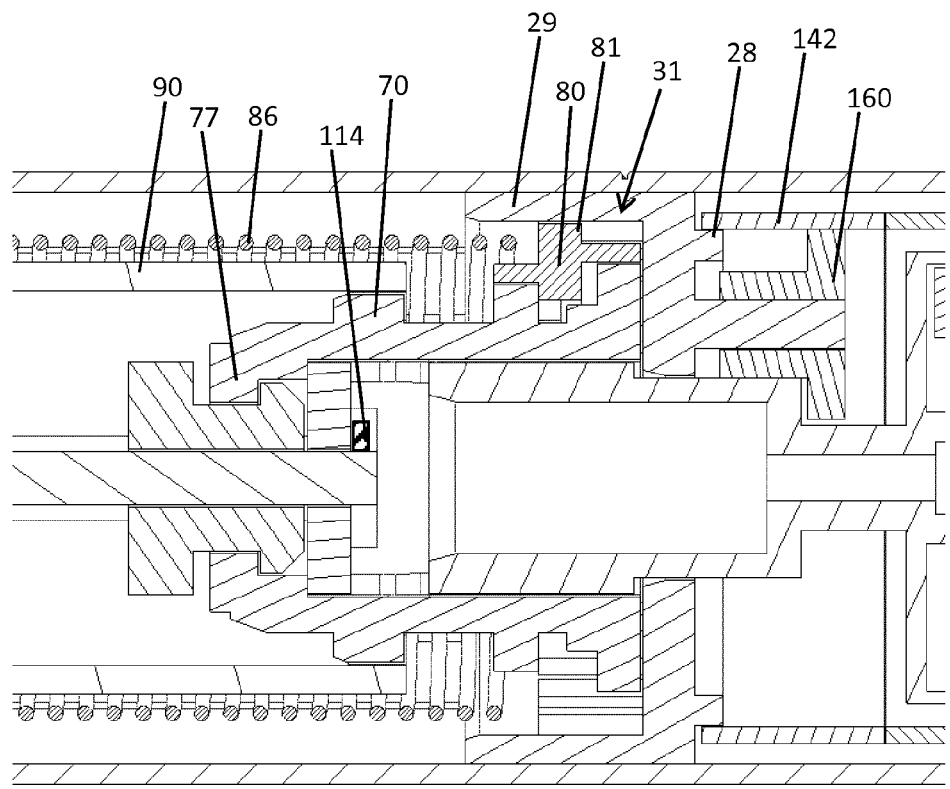
FIG. 14 shows an enlarged view of the drive sleeve in the configuration according to FIG. 12.
Figure 15:
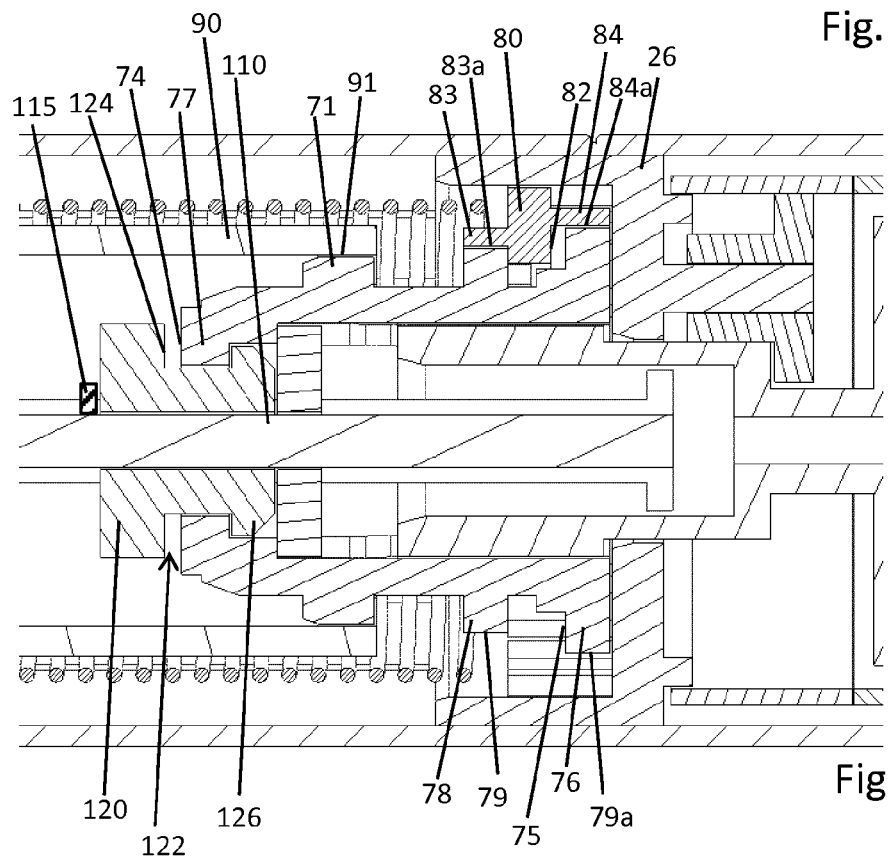
FIG. 15 shows an enlarged view of the drive sleeve in the configuration according to FIG. 13.

The drive sleeve 70 as illustrated in detail in FIGS. 8, 14 and 15 comprises a radially inwardly extending flange portion 77 at a distal end. Said radially extending flange portion 77 is located in a radial recess 122 of a drive member 120. The drive member 120 serves as a drive nut and features a central bore with an inner thread 121 by way of which it is threadedly engaged with the outer thread 111 of the piston rod 110. As indicated in FIGS. 14 and 15, the piston rod 110 axially extends through the drive member 120 and extends into the drive sleeve 70. The recess 122 of the drive member 120 comprises an axial extension that is larger than the axial width of the drive sleeve's 70 distal flange portion 77. In this way, the drive sleeve 70 can be axially displaced relative to the drive member 120, in particular for switching the drive mechanism 3 between a dose dispensing and a dose setting mode.

Figure 18:
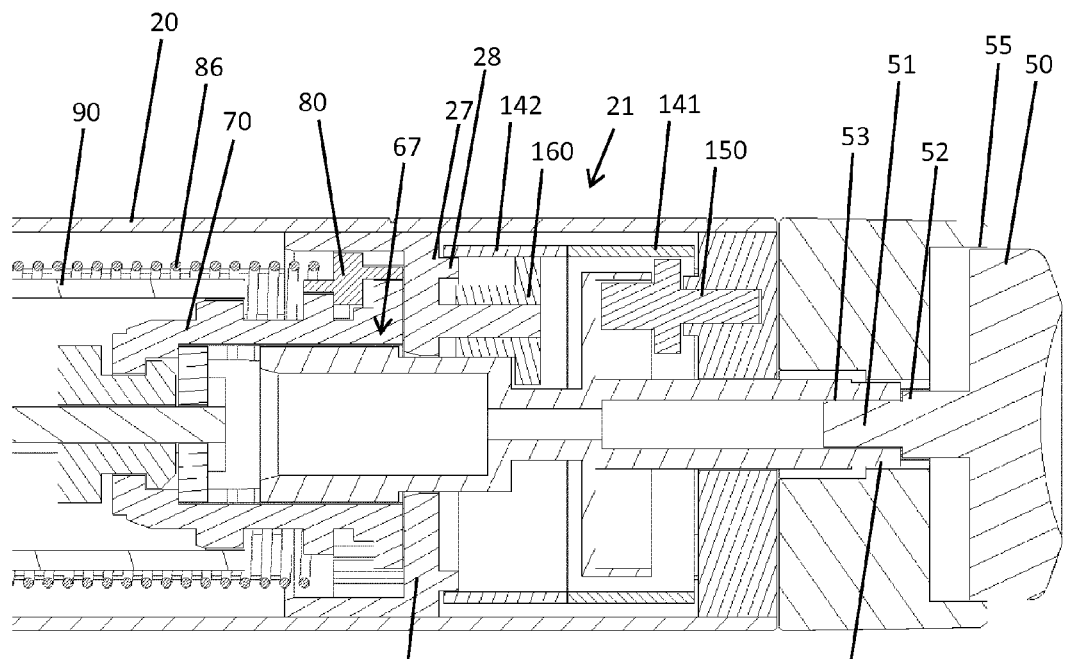
FIG. 18 shows a longitudinal cut through the drive mechanism in the dose setting mode

The drive member 120 comprises a radially widened head 126 that is located proximal to the radially inwardly extending distal flange portion 77 of the drive sleeve 70. The radially widened head 126 is wider than the through opening of the distal flange portion 77, so that drive sleeve 70 and drive member 120 are axially engaged in such a way, that the drive sleeve 70 axially constricted and is displaceable relative to the drive member 120 between a proximal stop position as indicated in FIG. 18 and a distal stop position as shown in FIG. 19.

Additionally, the distal end face of the drive sleeve 70 comprises a crown wheel 74 that matches with a correspondingly shaped crown wheel 124 of the drive member 120. Typically, the crown wheel 124 of the drive member 120 is located on a radially widened portion of the drive member 120.

Figure 19:
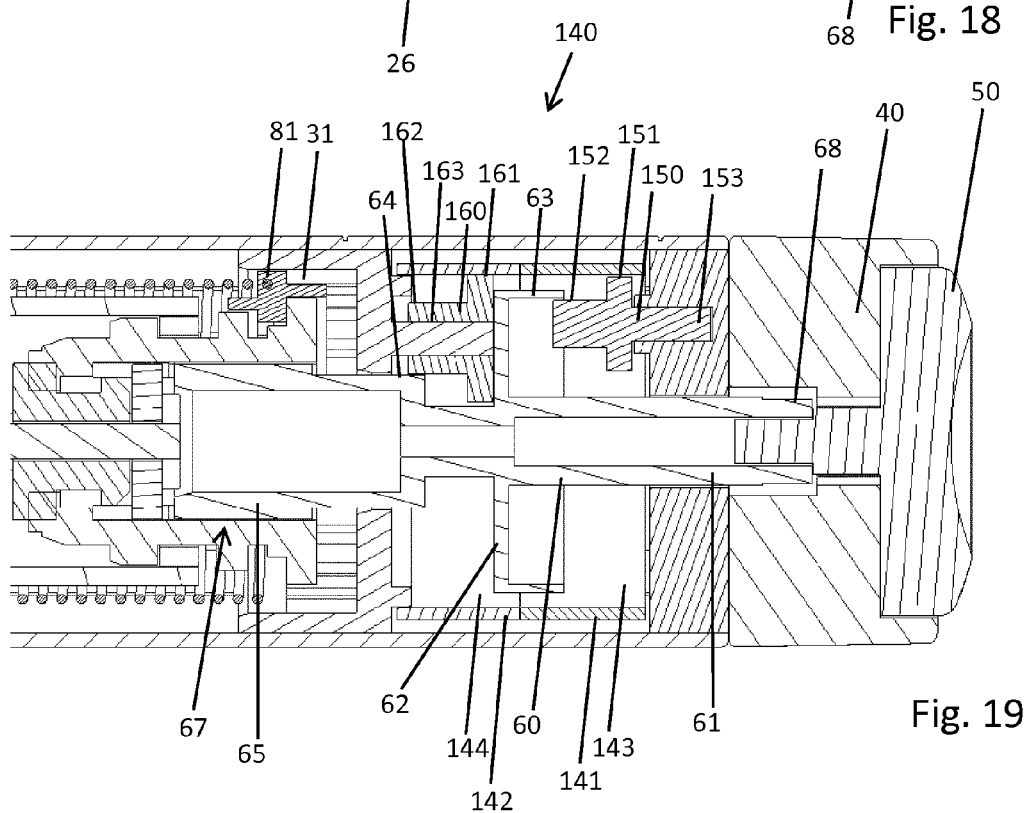
FIG. 19 shows the drive mechanism in dose dispensing mode.

When the drive sleeve 70 is in its distal stop position as shown in FIG. 19, the crown wheels 74, 124 of drive sleeve 70 and drive member 120 mutually engage in a torque transferring way. In this way, a rotation of the drive sleeve 70 is equally transferable into a respective rotation of the drive member 120. Due to the threaded engagement of piston rod 110 and drive member 120, a dose decrementing rotation of the drive member 120 during dose dispensing transfers into a distally directed displacement of the piston rod 110 relative to the body 20 and hence relative to the cartridge holder 13 and the cartridge 12, thus leading to a respective displacement of the piston 14 relative to the cartridge 12 thereby expelling a predefined dose of the medicament.

The drive sleeve 70 further comprises a proximal flange portion 76 at its proximal end. By means of the radially outwardly extending proximal flange portion 76 the drive sleeve 70 axially abuts with the distal base member 26, as indicated in FIG. 15. At a distally facing portion the proximal flange portion 76 comprises a second crown wheel 75 or a respective toothing that is selectively engageable with a corresponding crown wheel 82 or toothing of the blocking member 80.

The blocking member 80 further comprises a proximally extending rim portion having a gliding surface 84a facing radially inwardly. Additionally, the blocking member 80 also comprises a distally extending rim portion 83 with a radially inwardly facing gliding surface 83a. As indicated for instance in FIG. 15, the distal rim portion 83 is radially supported by an intermediate and radially outwardly extending flange portion 78 of the drive sleeve 70 featuring a gliding surface 79.

Additionally, the proximal rim portion 84 is radially supported by the proximal flange portion 76 of the drive sleeve 70 having a respective outer gliding surface 79a. The blocking member 80 further comprises a radially outwardly extending toothing 81 to engage with a correspondingly shaped toothing 31 provided at an inward facing sidewall portion of the distal base member 26 as illustrated in FIG. 3. When the toothings 81, 31 mutually engage as it is the case in the dose setting configuration shown in FIGS. 14, 15 and 18, the blocking member 80 is rotatably fixed to the proximal base member 26 and hence to the body 20.

It is upon a distally directed displacement of the blocking member 80, that the toothings 81, 31 disengage as shown in FIG. 19, thereby allowing the blocking member 80 to rotate under the action of the relaxing helical spring element 86. The blocking member 80 is displaceable in distal direction 1 by means of the drive sleeve 70. In the dose setting mode as for instance indicated in FIG. 18, the drive sleeve 70 is free to rotate relative to the blocking member 80. Here, the gliding surface 79 of the drive sleeve 70 glides along the gliding surface 83a of the blocking member 80. Additionally, also the gliding surface 79a of the drive sleeve 70 slides or glides along the correspondingly and even shaped gliding surface 84a of the blocking member 80.

A rotation of the drive sleeve 70 in the dose setting mode as illustrated in FIGS. 14, 15 and 18 further transfers into a respective rotation of the retraction member 90 by means of the mutually corresponding toothings 71, 91 of the drive sleeve 70 and the retraction member 90, respectively.

The drive sleeve 70 as shown in cross-section in FIG. 3 further comprises radially outwardly extending recesses 73 to receive correspondingly shaped radially outwardly extending protrusions 66 provided on the distal shaft portion 65 of the clutch member 60. Additionally but not illustrated here, the clutch member 60, which is inserted into the proximal end portion of the drive sleeve 70 is also axially fixed to the drive sleeve 70, e.g. by means of some kind of snap fit engagement, symbolized by a fixing member 67 in FIGS. 18 and 19. In this way, any rotational or axial displacement of the clutch member 60 equally transfers to the drive sleeve 70 and vice versa.

Figure 7:
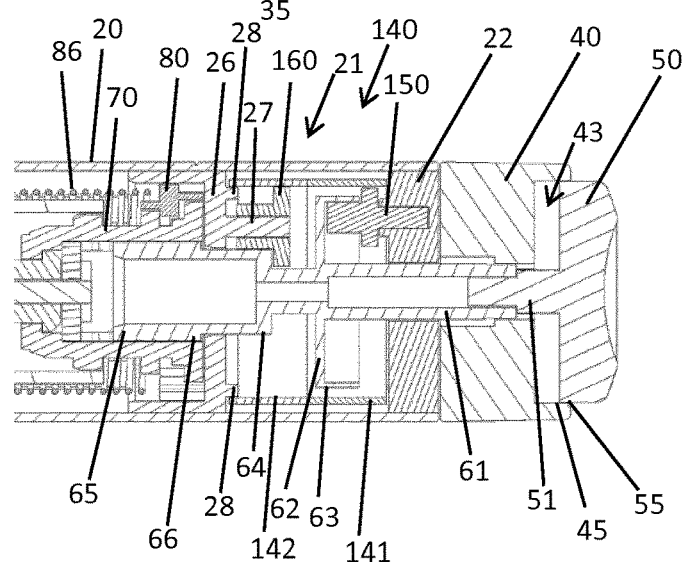
FIG. 7 shows a longitudinal cross-section of the proximal end of the drug delivery device.

The clutch member 70 is axially guided and radially supported by the proximal base member 22 and in the distal base member 26. Additionally, the clutch member 60 comprises a proximal shaft portion 61. As indicated in FIG. 7 as well as in FIGS. 18 and 19, the hollow proximal shaft portion 61 receives a distally extending central shaft portion 51 of a dose dispensing member 50. The button-shaped dose dispensing member 50 features a stepped portion 52 in its shaft portion 51 such that the stepped portion 52 axially abuts with a proximal end of the proximal shaft portion 68 of the clutch member 60.

Additionally and as indicated in FIG. 18, the dose dispensing member's shaft portion 51 comprises a fixing member 53, axially engaged with the clutch member 60. The fixing member 53 may comprise a resilient latch element to engage with a corresponding recessed portion of the clutch member 60, or vice versa. By means of the fixing member 53 the clutch element 60 and the dose dispensing member 50 are axially fixed so that any axially directed displacement of the dose dispensing member 50 is transferred to clutch member 60, and vice versa.

In this way, a distally directed displacement of the dose dispensing member 50 can be unalterably transferred to the clutch member 60 and hence to the drive sleeve 70. Typically, the distally directed displacement of the dose dispensing member 50 and/or of the clutch member 60 may act against the action of a retention spring element which is not particularly illustrated here. Typically, such spring element could be integrally formed in the clutch member 60. It may be further supported on or at a proximal end face of the proximal base member 22. A release of the dose dispensing member 50, e.g. during or at the end of a dose dispensing procedure may then lead to an immediate proximally directed displacement of the clutch member 60 in order to switch the drug delivery device 10 into the dose setting mode.

Figure 2:
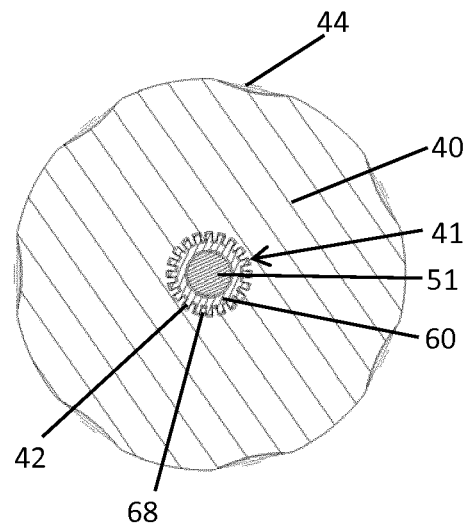
FIG. 2 shows a cross-section along A-A according to FIG. 1.

As further indicated in FIG. 2, the clutch member 60 comprises a toothing 68 at its proximal end engaged with a corresponding toothing 42 of a dose setting member 40. The dose setting member 40 of tubular or knob-like shape features a central through opening 41 to receive the proximal shaft portion 61 of the clutch member 60 as well as to receive the distally extending shaft portion 51 of the dose dispensing member 50. The dose setting member 40 is further axially supported by the base member 22. It may be axially fixed to the base member 22 and may form a proximal end of the housing and hence of the drug delivery device 10.

The dose setting member 40 further comprises a rippled gripping surface 44 along its outer circumference as indicated in FIG. 2. Furthermore, as illustrated in FIG. 7 it comprises a cylindrically-shaped receptacle 43 at its proximal end face to receive the outer circumference of the dose dispensing member 50. Since the dose setting member 40 is rotatably engaged via the toothing 42 with the clutch member 60, a rotation of the dose setting member 40 equally transfers to the clutch member 60 and hence to the drive sleeve 70 interconnected therewith.

Additionally but not necessarily the outer circumference of the button shape dose setting member 50 also comprises a toothing 55 that is in engagement with a correspondingly shaped toothing 45 of an inward facing sidewall of the dose setting member's 40 receptacle 43. In this way, the dose dispensing member 50 rotates in unison with the dose setting member 40 during a dose setting procedure.

However, when depressing the dose dispensing member 50 in distal direction 1, the clutch member 60 is displaced in distal direction 1 accordingly, thereby disengaging the toothing 68 of the clutch member 60 from the toothing 41 of the dose setting member 40. In this way, and during dose dispensing, the dose setting member 40 may be further rotatable. Since the rotational engagement of dose setting member 40 and clutch member 60 is abrogated a rotation or dialing of the dose setting member 40 during dose dispensing is substantially effectless.

The clutch member 60 is further permanently engaged with the display assembly 140. As illustrated in FIGS. 18 and 19, the display assembly 140 comprises a first dose indicating member 141 and a second dose indicating member 142. Both sleeve-shaped dose indicating members 141, 142 comprise an inner toothing 143, 144, respectively. Radially outwardly, hence at its outer circumference, the first dose indicating member 141 comprises a first display surface 145 adapted to illustrate various digits 0, . . . , 9, whereas the second dose indicating member 142 comprises a second display surface 146 adapted to display consecutive digits 1, . . . , 12.

In this way, the combination of first and second dose indicating members 141, 142 is applicable to illustrate consecutive numbers from 0-120, thereby representing e.g. 0-120 IU. The first wheel 150 as illustrated comprises a proximally extending central shaft 153 located in a correspondingly shaped receptacle or blind hole 23 of the proximal base member 22. The first wheel 150 further comprises a first geared rim 151 that meshes with the toothing 143 on the inside facing sidewall portion of the first dose indicating member 141.

Axially adjacent to said first geared rim 151, the first wheel 150 comprises a second geared rim 152, which is reduced in diameter compared to the first geared rim 151. The outer circumference of the second geared rim 152 is engaged and meshes with an inwardly facing toothing or with a respective inner gear axially extending at the radially outwardly located portion of a disc-shaped flange portion 62 of the clutch member 60. Said radially outwardly extending disc-like flange portion 62 of the clutch member 60 further provides axial abutment for the second wheel 160 that features a central bore 163 to receive a proximally extending shaft 27 of the distal base member 26.

Also the second wheel 160 is provided with a geared rim 162, which directly meshes with an outer gear 64 of the clutch member 60. But in contrast to the first wheel 150, the second wheel 160 is engaged with the second dose indicating member 142 by means of a single or several isolated tappets 161, only frequently meshing with the toothing 144 of the second dose indicating member 142. For instance, the second wheel 160 comprises only one tappet or two diametrically oppositely located tappets radially outwardly extending from the outer circumference of the second wheel 160.

Then, during a complete revolution of the second wheel 160, said tappet 161 only engages once or twice with the toothing 144 of the second dose indicating member 142. In this way, the second dose indicating member 142 is stepwise rotated in discreet steps every time the first display surface 145 changes from 9 to 0 when dialed in a dose incrementing direction 5, as for instance illustrated in FIG. 11.

The distal base member 26 further comprises a proximally extending retaining member 28 engaging with the sidewall portion of the second dose indicating member 142. In particular, the second dose indicating member 142 may comprise radially extending notches to receive or to engage with the retaining member 28. In this way and in situations in which the tappet 161 is not in engagement with the second dose indicating member 142 the second dose indicating member 142 is substantially immobilized or fixed to the body 20.

In effect, the first dose indicating member 141 represents single digits or the last digit of a two or three digit number whereas the second dose indicating member 142 is operable to represent the first or the first and the second digits of a two or three digit number. Hence, the second display surface 146 of the second dose indicating member 142 represents integer multiples of ten, and hence numbers such like 10, 20, 30, . . . , 120.

As becomes apparent from FIGS. 18 and 19, the axial extension of the inner gear 63 and the outer gear 64 is larger than the maximum axial displacement path of the clutch member 60. In this way, the clutch member 60 remains permanently engaged with the first and second wheels 150, 160. Consequently, any rotation of the clutch member 60 leads to a respective dose incrementing or dose decrementing rotation of the first and the second dose indicating members 141, 142.

In the following, setting of a dose is described.

Figure 11:
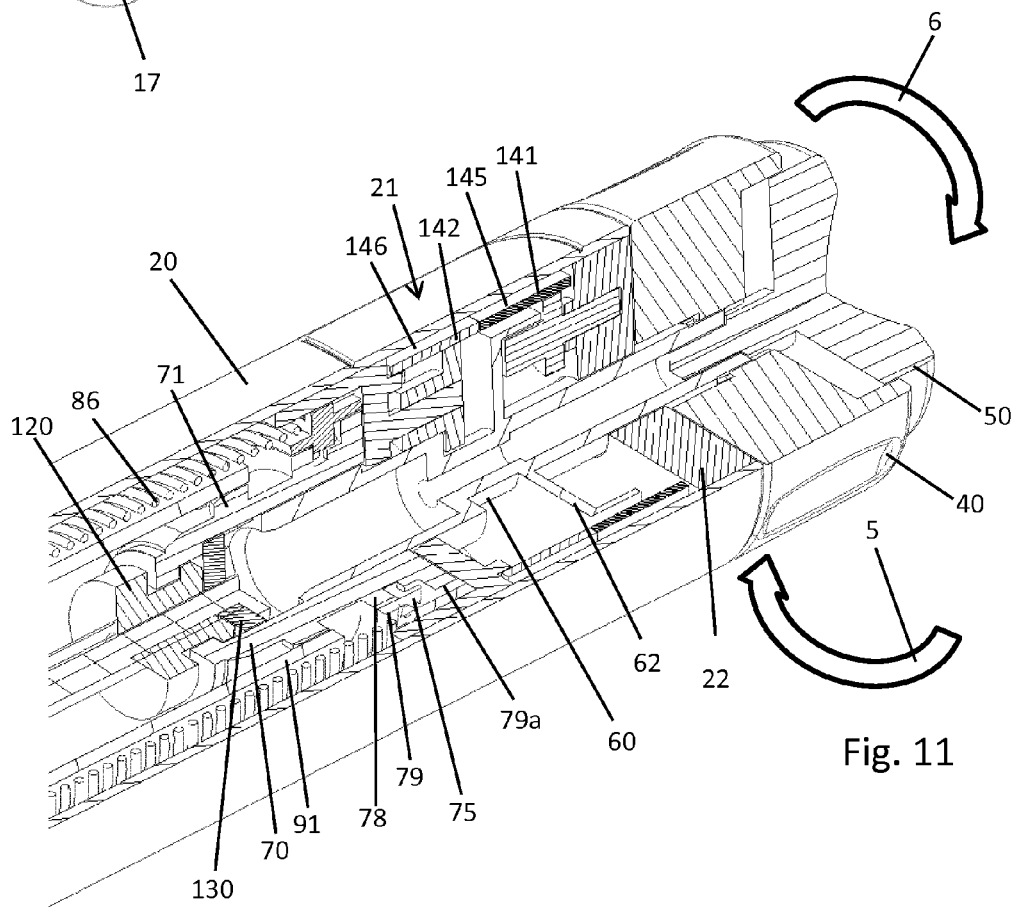
FIG. 11 shows a partially cut and perspective illustration of the proximal end of the drug delivery device.

Per default the drug delivery device 10 is in dose dispensing mode as for instance illustrated in FIGS. 12, 13 and 18. When a user starts dialing the dose setting member 40 in a dose incrementing direction 5 as indicated in FIG. 11, the rotation of the dose setting member 40 is equally transferred to the clutch member 60 via the mutually corresponding toothings 42, 68 of dose setting member 40 and clutch member 60, respectively.

The respective rotation of the clutch member 60 transfers to the two wheels 150, 160 of the display assembly 140. Accordingly, respective dose indicating numbers of the first and second display surfaces 145, 146 will show up in the window 21 of the body. Additionally, the rotation of the clutch member 60 is equally transferred to the drive sleeve 70 and to the retraction member 90 via the mutually corresponding toothings 71, 91 of drive sleeve 70 and retraction member 90, respectively. A rotation of the retraction member 90 in dose incrementing direction 5 leads to a retraction of the coupling member 100 and hence to a respective proximally directed retraction of the cartridge holder 13 as becomes apparent from FIG. 13.

Since the piston rod 110 with its distal pressure piece 113 is in direct axial abutment with a proximal end face of the piston 14, also the piston rod 110 is translationally displaced in proximal direction 2 relative to the drive member 120 and relative to the drive sleeve 70. A proximally directed displacement of the piston rod 110 relative to the drive member 120 is possible when the drive member 120 rotates in unison with the drive sleeve 70 during dose setting. Moreover, the threaded engagement of the coupling member 100 and the retraction member 90 may comprises a pitch equal to the threaded engagement of piston rod 110 and drive member 120. In an alternative embodiment the threaded engagement of piston rod 110 and drive member 120 may be of non-self-locking type. Hence a proximally directed axial displacement of the piston rod as it is induced through a dose increasing rotation of the drive sleeve 70 leads to a rotation of the drive member 120. Here, the drive member 120 may be rotatably decoupled from the drive sleeve 70 and may rotate independently from the drive sleeve, i.e. with a different angular velocity.

The piston rod 110 as illustrated in FIG. 15 axially enters the distal shaft portion 65 of the clutch member 60 as indicated in FIG. 15. A proximally directed displacement of the piston rod 110 is delimited by a distal stop 115 provided at the outer circumference of the piston rod as indicated in FIG. 15. Said distal stop 150 may either axially and/or radially engage with a correspondingly shaped but not illustrated stop of the drive member 120. When mutually corresponding stops of drive member 120 and piston rod 110 get in abutment, a further dose incrementing rotation of the drive member 120 relative to the piston rod 110 is substantially inhibited, thus leading to a blocking of the rotation of the drive sleeve 70, of the clutch member 60 and hence of the dose setting member 40.

As indicated in FIG. 14 the piston rod 110 further comprises another radially extending proximal stop 114 at a proximal end portion. Said proximal stop 110 is adapted to engage with a correspondingly shaped stop of a single dose limiting member 130 as illustrated in FIG. 14. Said single dose limiting member 130 is operable to prevent dialing of a negative dose and to stop a distally directed displacement of the piston rod 110 during or at the end of a dose dispensing procedure.

The single dose limiting member 130 is of disc-like shape and comprises two radially outwardly extending protrusions 132 engaged with two correspondingly shaped axially extending grooves or recesses 72 of the drive sleeve 70. In this way, the single dose limiting member 130 is permanently rotatably engaged with the drive sleeve 70 but is allowed to axially move relative to the drive sleeve 70. The single dose limiting member 130 also comprises a central bore through which the threaded piston rod 110 extends in axial direction.

The outer thread 111 of the piston rod 110 is threaded with a correspondingly shaped inner thread 131 of the single dose limiting member 130. The pitch of the threaded engagement of the single dose limiting member 130 and the piston rod 110 might be also equal to the pitch of the threaded engagement of the drive member 120 and the piston rod 110. It is also equal to the pitch of the threaded engagement of the coupling member 100 and the retraction member 90.

Given that a selected dose is too large, the dose setting member 40 can be rotated in the opposite direction, hence in dose decrementing direction 6 as indicated in FIG. 11. Then, the rotatable components as mentioned above will rotate in the opposite direction, thus leading to an axial displacement of the coupling member 100 and the piston rod 110 together with the cartridge 12 in distal direction 1. Accordingly, the dose indicating numbers showing up in the window 21 will decrement. Once a dose has been correctly set, the drug delivery device 10 is ready for dose dispensing.

In the following, dispensing of a dose will be described.

Dispensing of a dose is simply triggered by depressing the dose dispensing member 50 in distal direction 1 as becomes apparent from a comparison of FIGS. 18 and 19. The distally directed displacement of the dose dispensing member 50 leads to a corresponding displacement of the clutch member 60 and of the drive sleeve 70 connected therewith. Consequently, the toothing 68 of the clutch member 60 disengages from the correspondingly shaped toothing 42 of the dose setting member 40.

Hence, any further rotation of the dose setting member 40 is substantially effectless when the dose dispensing procedure in progress. The distally directed displacement of the drive sleeve 70 leads to a decoupling or disengagement of drive sleeve 70 and retraction member 90. Consequently, during dose dispensing the cartridge holder 13 will remain in its position.

Furthermore, by displacing the drive sleeve 70 in distal direction 1, the crown wheel 75 located at the proximal flange portion 76 of the drive sleeve 70 engages with the correspondingly shaped crown wheel 82 of the blocking member 80 facing in proximal direction 2. In this way, blocking member 80 and drive sleeve 70 are rotatably interlocked. Shifting further of the drive sleeve 70 towards its distal stop position then leads to a corresponding distally directed displacement of the blocking member 80.

Consequently, the toothing 81 of the blocking member 80 disengages from the toothing 31 of the body 20. In this way, the blocking member 80 is free to rotate under the action of the relaxing helical spring element 86 that is permanently connected to the blocking member 80. Since the blocking member 80 is rotatably interlocked or rotatably engaged with the drive sleeve 70 also the drive sleeve 70 starts to rotate in a dose decrementing direction 6. Additionally and prior to a release of the blocking member 80 from the body 20, the drive sleeve 70 also rotatably engages with the drive member 120.

Here, the distal crown wheel 74 of the drive sleeve 70 engages with the correspondingly shaped crown wheel 124 of the drive member 120 facing in proximal direction. In this way, the spring-induced rotation of the blocking member 80 and of the drive sleeve 70 equally transfers to a respective rotation of the drive member 120. Since the piston rod 110 threadedly engaged with the drive member 120 is rotatably interlocked with the coupling member 110 via its longitudinally extending groove 112 the piston rod 110 cannot rotate but is driven in distal direction instead until the initial configuration as illustrated in FIG. 14 is reached, in which the proximal stop 114 of the piston rod 110 engages with the single dose limiting member 130.

Reaching of this initial configuration may be further accompanied by a visual or audible feedback. For instance, the proximal stop 114 and the single dose limiting member 130 may audibly engage, e.g. by way of a particular click sound generating element, such like a resilient latch element. In this way, the end of a dispensing procedure can be audibly indicated to a user.

When releasing the dose dispensing member 50 during or after termination of a dose dispensing procedure, an axially acting retraction spring, e.g. located between the clutch member 60 and one of the proximal base member 22 or distal base member 26 serves to immediately displace the clutch member 60 in proximal direction 2. Since the clutch member 60 is also axially interlocked or axially connected to the drive sleeve 70, the proximally directed retraction of the clutch member 60 equally transfers to the drive sleeve 70.

Consequently, since the drive member 120 is threadedly engaged with the piston rod 110, the crown wheels 74, 124 of the drive sleeve 70 and of the drive member 120 will immediately disengage, thereby interrupting any further distally directed displacement of the piston rod 110. With the proximally directed retraction of the drive sleeve 70 also the blocking member 80 returns into its proximal stop position as indicated in FIG. 18. Here, the intermediate flange portions 78 of the drive sleeve 70 may serve to exert a respective axially and proximally directed displacement force to the blocking member 80. Additionally, it is conceivable, that the blocking member 80 returns into its proximal stop position under the effect of the helical spring 86.

For not losing mechanical energy stored in the helical spring 86 it is of particular benefit that the drive sleeve 70 consecutively engages and disengages with the drive member 120 and the blocking member 80 as described in the following. For switching the drive mechanism 3 from dose setting mode as illustrated in FIG. 18 into dose dispensing mode as shown in FIG. 19, the drive sleeve 70 is displaced in distal direction 1.

During this distally directed displacement of the drive sleeve 70, the drive sleeve first engages with the drive member 120 before the blocking member 80 disengages from the body 20. Additionally, the drive sleeve 70 should disengage from the retraction member 90 before the blocking member 80 is released to rotate under the action of the helical spring 86. When releasing the button-shaped dose dispensing member 50 engagement and disengagement of drive sleeve 70, retraction member 90, drive member 120, blocking member 80 and body 20 or distal base member 26 should take place in the reverse order.

The single dose limiting member 130 is axially shiftable relative to the drive sleeve 70 which is of particular benefit during switching of the drive mechanism 3 between dose setting and dose dispensing mode as becomes apparent from the comparison of FIGS. 18 and 19. Generally, the single dose limiting member 130 is in axial abutment with a proximal end of the drive member 120. But since the drive member 120 is free to rotate relative to the drive sleeve 70 in the dose setting mode, it is the single dose limiting member 130 which effectively provides a rotational blocking of piston rod 110 and drive sleeve 70 in the zero dose configuration as illustrated in FIG. 14.

In the embodiment as illustrated, the blocking member 80 is either engaged with the body 20 via the distal base member 26 or it is engaged with the drive sleeve 70. In particular, since the blocking member 80 is operably disconnected from the drive sleeve 70 during dose setting, the dose setting can take place without any interaction with the helical spring 86. Moreover, when the helical spring 86 extending radially between the body 20 and the retraction member 90 is 'charged for life' sufficient energy can be provided to repeatedly transfer a driving torque to the drive sleeve 70 during subsequent dose dispensing procedures until an end of content configuration as shown in FIG. 17 has been reached.

The invention claimed is:

1. A drug delivery device for dispensing of a dose of a medicament, the drug delivery device comprising:
   an elongated body;
   a cartridge holder to accommodate a cartridge that is at least partially filled with the medicament and has an axially displaceable piston;
   a piston rod to operably engage with the axially displaceable piston of the cartridge to displace the axially displaceable piston in a distal direction; and
   a coupling member connected with the cartridge holder and axially displaceably arranged in the elongated body for retracting the cartridge holder into the elongated body during dose setting,
   wherein the cartridge holder and the elongated body are slidingly and non-rotatably connected, wherein one of the elongated body and the cartridge holder comprises a radially extending protrusion, and wherein the other one of the elongated body and the cartridge holder comprises a radially extending recess, and
   wherein the elongated body and the cartridge holder are keyed by the radially extending protrusion engaged with the radially extending recess.

2. The drug delivery device according to claim 1, wherein the cartridge holder is rotationally fixed relative to the elongated body and is radially and axially guided by a through-opening at a distal end of the elongated body.

3. The drug delivery device according to claim 1, wherein the elongated body comprises the radially extending protrusion extending into the radially extending recess of the cartridge holder.

4. The drug delivery device according to claim 3, wherein the radially extending recess comprises a stop edge at a distal end of the radially extending recess to delimit a proximally directed displacement of the cartridge holder relative to the elongated body when the cartridge reaches an end-of-content configuration.

5. The drug delivery device according to claim 1, further comprising a drive sleeve rotatably supported in the elongated body and being operably engageable with the piston rod to induce a distally directed displacement of the piston rod for dispensing the dose.

6. The drug delivery device according to claim 5, further comprising a blocking member engaged with a pretensioned spring element and being alternately engageable with the elongated body or with the drive sleeve.

7. The drug delivery device according to claim 5, wherein the drive sleeve is axially displaceable between a proximal stop position and a distal stop position for switching between a dose setting mode and a dose dispensing mode.

8. The drug delivery device according to claim 5, wherein the piston rod is displaceable in a proximal direction relative to at least one of the elongated body and the drive sleeve during the dose setting.

9. The drug delivery device according to claim 5, further comprising:
- a single dose limiting member threadedly engaged with the piston rod, the dose limiting member being rotationally fixed relative to and axially displaceably engaged with the drive sleeve, and
- a sleeve-shaped retraction member rotatably supported in the elongated body and being threadedly engaged with the coupling member,
- wherein the drive sleeve is rotatably engageable with a drive member, the drive member threadedly engaged with the piston rod, and
- wherein at least two of a threaded engagement of the coupling member and the sleeve-shaped retraction member, a threaded engagement of the piston rod and the drive member, or a threaded engagement of the piston rod and the single dose limiting member comprise an equal pitch.

10. The drug delivery device according to claim 5, wherein the drive sleeve is rotatably engageable with a drive member, the drive member threadedly engaged with the piston rod.

11. The drug delivery device according to claim 5, further comprising a single dose limiting member threadedly engaged with the piston rod and rotationally fixed relative to and axially displaceably engaged with the drive sleeve.

12. The drug delivery device according to claim 5, further comprising a sleeve-shaped retraction member rotatably supported in the elongated body and threadedly engaged with the coupling member.

13. The drug delivery device according to claim 12, wherein the drive sleeve and the sleeve-shaped retraction member are rotatably coupled during the dose setting, and the drive sleeve and the sleeve-shaped retraction member are rotatably disengaged during dose dispensing.

14. The drug delivery device according to claim 1, wherein the piston rod axially extends through a through-opening of the coupling member.

15. The drug delivery device according to claim 1, further comprising the cartridge, the cartridge being arranged in the cartridge holder and containing at least one pharmaceutically active compound.

16. A drug delivery device for dispensing of a dose of a medicament, comprising:
- an elongated body;
- a cartridge holder to accommodate a cartridge that is at least partially filled with the medicament and has an axially displaceable piston;
- a piston rod to operably engage with the axially displaceable piston of the cartridge to displace the axially displaceable piston in a distal direction;
- a coupling member connected with the cartridge holder and axially displaceably arranged in the elongated body for retracting the cartridge holder into the elongated body during dose setting;
- a drive sleeve rotatably supported in the elongated body and being operably engageable with the piston rod to induce a distally directed displacement of the piston rod for dispensing of the dose; and
- a sleeve-shaped retraction member rotatably supported in the elongated body and being threadedly engaged with the coupling member,
- wherein the drive sleeve and the sleeve-shaped retraction member are rotatably coupled during the dose setting, and the drive sleeve and the sleeve-shaped retraction member are rotatably disengaged during dose dispensing.

17. A drug delivery device for dispensing of a dose of a medicament, the drug delivery device comprising:
- an elongated body;
- a cartridge holder to accommodate a cartridge that is at least partially filled with the medicament and has an axially displaceable piston;
- a piston rod to operably engage with the axially displaceable piston of the cartridge to displace the axially displaceable piston in a distal direction;
- a coupling member connected with the cartridge holder and axially displaceably arranged in the elongated body for retracting the cartridge holder into the elongated body during dose setting;
- a drive sleeve rotatably supported in the elongated body and being operably engageable with the piston rod to induce a distally directed displacement of the piston rod for dispensing the dose;
- a single dose limiting member threadedly engaged with the piston rod, the dose limiting member being rotationally fixed relative to and axially displaceably engaged with the drive sleeve; and
- a sleeve-shaped retraction member rotatably supported in the elongated body and being threadedly engaged with the coupling member,
- wherein the drive sleeve is rotatably engageable with a drive member threadedly engaged with the piston rod, and
- wherein at least two of a threaded engagement of the coupling member and the sleeve-shaped retraction member, a threaded engagement of the piston rod and the drive member, and a threaded engagement of the piston rod and the single dose limiting member comprise an equal pitch.

\* \* \* \* \*